United States Patent [19]

Jacobson et al.

[11] Patent Number: 5,599,671
[45] Date of Patent: Feb. 4, 1997

[54] HUMAN A2B ADENOSINE RECEPTOR ASSAY

[75] Inventors: Marlene A. Jacobson, Elkins Park; Christopher J. Luneau, Lansdale; Robert G. Johnson, Rosemont; Christopher A. Salvatore, North Wales, all of Pa.

[73] Assignee: Merck & Co., Inc., Rahway, N.J.

[21] Appl. No.: 349,696

[22] Filed: Dec. 5, 1994

Related U.S. Application Data

[63] Continuation of Ser. No. 5,945, Jan. 15, 1993, abandoned, which is a continuation-in-part of Ser. No. 850,702, Mar. 13, 1992, abandoned, and Ser. No. 850,701, Mar. 13, 1992, abandoned, and Ser. No. 850,707, Mar. 13, 1992, abandoned.

[51] Int. Cl.$^6$ .............................. C12N 5/10; C12N 15/12
[52] U.S. Cl. .............................. 435/6; 435/7.2; 435/7.21; 435/69.1; 435/252.3; 435/320.1; 536/23.5
[58] Field of Search .............................. 435/6, 7.2, 7.21, 435/69.1, 252.3, 320.1; 436/501; 536/23.5

[56] References Cited

U.S. PATENT DOCUMENTS 5,441,883  8/1995  Civelli et al. ........................ 435/257 D

OTHER PUBLICATIONS

Zhou, Q.-Y. et al., "Molecular Cloning . . . of . . . A3 Adenosine receptor," Proc. Nat. Acad. Sci. 89, 7432 (1992).
Pierce, K. D. et al., "Molecular Cloning and Expression . . . ," Biochemical and Biophysical Research Communications, vol. 187, No. 1, 86–93 (1992).
Furlong, T. J. et al., "Molecular characterization of a human . . . " Molecular Brain Research, 15, 62–66 (1992).
Olah, M. E. et al., ". . . Characterization of . . . Bovine A, Adnosine Receptor," J. Biol. Chem. 267, 10764 (1992, Issue of May 25).
Chern, Y. et al., ". . . Cloning of . . . Adenosine Receptor Gene From Rat Brain," BBRC 185, 304 (1992).
Tiffany, H. L. et al., "Human Adenosine receptor (A2) gene . . . ," Gen Bank, Accession M97370 (Jul. 25, 1992) (3 pages).
Fink, J. S. et al., ". . . Cloning of the rat A2 adenosine receptor . . . ," Mol. Brain Res. 14, 186 (1992).
J. H. Stehle, et al; Molecular Cloning and Expression of the cDNA for a Novel $A_2$Adenosine Receptor Subtype, Molecular Endocrinology, No. 3, vol. 6, pp. 384–393 (Mar., 1992).
R. F. Bruns, et al., (1983) Proc. Natl. Acad. Sci. USA 80:2077–2080.
R. F. Bruns, et al., (1986) Mol. Pharmacol. 29:331–346.
K. A. Jacobson, et al., (1989) J. Med. Chem 32:1043–1051.
M. F. Jarvis, et al., (1989) J. Pharma, Esp. Therap. 251:888–893.
F. Libert, et al., (1989) Science 244:569–572.
F. Libert, et al., (1991) EMBO J. 10:1677–1682.
C. Maenhaut, et al., Biochem. Biophys. Res. Comm., (1990) 173:1169–1178.
L. C. Mahan, et al., (1991) Mol. Pharm. 40:1–7.
S. M. Reppert, et al., (1991) Mol. Endocrin, 5:1037–1048.
A. L. Tucker, et al (1992) FEBS vol. 297, 107–111.
Pharm. Ther. vol. 50:425–442, 1991 Jackson Structure and Function of G Protein Coupled Receptors.
Biochem Biophys. Res. Comm. 173:1169–78 (Dec. 31, 1990) Maenhaut et al RDC8 Codes for an adenosine A2 receptor with physiological Constitutive Activity.
Science 244:569–572 (May 5 1989) Libert et al. Selective Amplification and Cloning of Four New Members of the G Protein–Coupled Receptor Family.

*Primary Examiner*—John Ulm
*Attorney, Agent, or Firm*—Richard S. Parr; Melvin Winokur

[57] ABSTRACT

The invention concerns recombinant human adenosine receptors A1, A2a, A2b and A3 which have been prepared by cDNA cloning and polymerase chain reaction techniques. The invention also concerns expression systems for these receptors and an assay using the expression systems. The recombinant adenosine receptors comprising the invention can be utilized in an assay to identify and evaluate entities that bind to or enhance binding to adenosine receptors.

1 Claim, 12 Drawing Sheets

Met Pro Pro Ser Ile Ser Ala Phe Gln Ala Ala Tyr Ile Gly Ile Glu
1           5               10              15

Val Leu Ile Ala Leu Val Ser Val Pro Gly Asn Val Leu Val Ile Trp
            20              25              30

Ala Val Lys Val Asn Gln Ala Leu Arg Asp Ala Thr Phe Cys Phe Ile
            35              40              45

Val Ser Leu Ala Val Ala Asp Val Ala Val Gly Ala Leu Val Ile Pro
    50              55              60

Leu Ala Ile Leu Ile Asn Ile Gly Pro Gln Thr Tyr Phe His Thr Cys
65              70              75              80

Leu Met Val Ala Cys Pro Val Leu Ile Leu Thr Gln Ser Ser Ile Leu
                85              90              95

Ala Leu Leu Ala Ile Ala Val Asp Arg Tyr Leu Arg Val Lys Ile Pro
            100             105             110

Leu Arg Tyr Lys Met Val Val Thr Pro Arg Arg Ala Ala Val Ala Ile
        115             120             125

Ala Gly Cys Trp Ile Leu Ser Phe Val Val Gly Leu Thr Pro Met Phe
    130             135             140

Gly Trp Asn Asn Leu Ser Ala Val Glu Arg Ala Trp Ala Ala Asn Gly
145             150             155             160

Ser Met Gly Glu Pro Val Ile Lys Cys Glu Phe Glu Lys Val Ile Ser
            165             170             175

Met Glu Tyr Met Val Tyr Phe Asn Phe Phe Val Trp Val Leu Pro Pro
            180             185             190

Leu Leu Leu Met Val Leu Ile Tyr Leu Glu Val Phe Tyr Leu Ile Arg
        195             200             205

FIG. 1A

Lys Gln Leu Asn Lys Lys Val Ser Ala Ser Ser Gly Asp Pro Gln Lys
    210                 215                 220

Tyr Tyr Gly Lys Glu Leu Lys Ile Ala Lys Ser Leu Ala Leu Ile Leu
225                 230                 235                 240

Phe Leu Phe Ala Leu Ser Trp Leu Pro Leu His Ile Leu Asn Cys Ile
            245                 250                 255

Thr Leu Phe Cys Pro Ser Cys His Lys Pro Ser Ile Leu Thr Tyr Ile
            260                 265                 270

Ala Ile Phe Leu Thr His Gly Asn Ser Ala Met Asn Pro Ile Val Tyr
        275                 280                 285

Ala Phe Arg Ile Gln Lys Phe Arg Val Thr Phe Leu Lys Ile Trp Asn
    290                 295                 300

Asp His Phe Arg Cys Gln Pro Ala Pro Pro Ile Asp Glu Asp Leu Pro
305                 310                 315                 320

Glu Glu Arg Pro Asp Asp
            325

FIG. 1B

```
                10                            30                            50
ATGCCGCCCT CCATCTCAGC TTTCCAGGCC GCCTACATCG GCATCGAGGT GCTCATCGCC
                70                            90                           110
CTGGTCTCTG TGCCCGGGAA CGTGCTGGTG ATCTGGGCGG TGAAGGTGAA CCAGGCGCTG
               130                           150                           170
CGGGATGCCA CCTTCTGCTT CATCGTGTCG CTGGCGGTGG CTGATGTGGC CGTGGGTGCC
               190                           210                           230
CTGGTCATCC CCCTCGCCAT CCTCATCAAC ATTGGGCCAC AGACCTACTT CCACACCTGC
               250                           270                           290
CTCATGGTTG CCTGTCCGGT CCTCATCCTC ACCCAGAGCT CCATCCTGGC CCTGCTGGCA
               310                           330                           350
ATTGCTGTGG ACCGCTACCT CCGGGTCAAG ATCCCTCTCC GGTACAAGAT GGTGGTGACC
               370                           390                           410
CCCCGGAGGG CGGCGGTGGC CATAGCCGGC TGCTGGATCC TCTCCTTCGT GGTGGGACTG
               430                           450                           470
ACCCCTATGT TTGGCTGGAA CAATCTGAGT GCGGTGGAGC GGGCCTGGGC AGCCAACGGC
               490                           510                           530
AGCATGGGGG AGCCCGTGAT CAAGTGCGAG TTCGAGAAGG TCATCAGCAT GGAGTACATG
               550                           570                           590
GTCTACTTCA ACTTCTTTGT GTGGGTGCTG CCCCCGCTTC TCCTCATGGT CCTCATCTAC
               610                           630                           650
CTGGAGGTCT TCTACCTAAT CCGCAAGCAG CTCAACAAGA AGGTGTCGGC CTCCTCCGGC
               670                           690                           710
GACCCGCAGA AGTACTATGG GAAGGAGCTG AAGATCGCCA AGTCGCTGGC CCTCATCCTC
               730                           750                           770
TTCCTCTTTG CCCTCAGCTG GCTGCCTTTG CACATCCTCA ACTGCATCAC CCTCTTCTGC
               790                           810                           830
CCGTCCTGCC ACAAGCCCAG CATCCTTACC TACATTGCCA TCTTCCTCAC GCACGGCAAC
               850                           870                           890
TCGGCCATGA ACCCCATTGT CTATGCCTTC CGCATCCAGA AGTTCCGCGT CACCTTCCTT
               910                           930                           950
AAGATTTGGA ATGACCATTT CCGCTGCCAG CCTGCACCTC CCATTGACGA GGATCTCCCA
               970
GAAGAGAGGC CTGATGACTA G
```

FIG. 2

Met Pro Ile Met Gly Ser Ser Val Tyr Ile Thr Val Glu Leu Ala Ile
1            5                    10                 15

Ala Val Leu Ala Ile Leu Gly Asn Val Leu Val Cys Trp Ala Val Trp
            20                  25                  30

Leu Asn Ser Asn Leu Gln Asn Val Thr Asn Tyr Phe Val Val Ser Leu
            35                  40                  45

Ala Ala Ala Asp Ile Ala Val Gly Val Leu Ala Ile Pro Phe Ala Ile
            50                  55                  60

Thr Ile Ser Thr Gly Phe Cys Ala Ala Cys His Gly Cys Leu Phe Ile
65                      70                  75                  80

Ala Cys Phe Val Leu Val Leu Thr Gln Ser Ser Ile Phe Ser Leu Leu
            85                  90                  95

Ala Ile Ala Ile Asp Arg Tyr Ile Ala Ile Arg Ile Pro Leu Arg Tyr
            100                 105                 110

Asn Gly Leu Val Thr Gly Thr Arg Ala Lys Gly Ile Ile Ala Ile Cys
            115                 120                 125

Trp Val Leu Ser Phe Ala Ile Gly Leu Thr Pro Met Leu Gly Trp Asn
    130                 135                 140

Asn Cys Gly Gln Pro Lys Glu Gly Lys Asn His Ser Gln Gly Cys Gly
145                 150                 155                 160

Glu Gly Gln Val Ala Cys Leu Phe Glu Asp Val Val Pro Met Asn Tyr
                165                 170                 175

Met Val Tyr Phe Asn Phe Phe Ala Cys Val Leu Val Pro Leu Leu Leu
            180                 185                 190

Met Leu Gly Val Tyr Leu Arg Ile Phe Leu Ala Ala Arg Arg Gln Leu
            195                 200                 205

FIG. 3A

Lys Gln Met Glu Ser Gln Pro Leu Pro Gly Glu Arg Ala Arg Ser Thr
210                     215                 220

Leu Gln Lys Glu Val His Ala Ala Lys Ser Leu Ala Ile Ile Val Gly
225                 230                 235                 240

Leu Phe Ala Leu Cys Trp Leu Pro Leu His Ile Ile Asn Cys Phe Thr
            245                 250                 255

Phe Phe Cys Pro Asp Cys Ser His Ala Pro Leu Trp Leu Met Tyr Leu
            260                 265                 270

Ala Ile Val Leu Ser His Thr Asn Ser Val Val Asn Pro Phe Ile Tyr
            275                 280                 285

Ala Tyr Arg Ile Arg Glu Phe Arg Gln Thr Phe Arg Lys Ile Ile Arg
290                 295                 300

Ser His Val Leu Arg Gln Gln Glu Pro Phe Lys Ala Ala Gly Thr Ser
305                 310                 315                 320

Ala Arg Val Leu Ala Ala His Gly Ser Asp Gly Glu Gln Val Ser Leu
                325                 330                 335

Arg Leu Asn Gly His Pro Pro Gly Val Trp Ala Asn Gly Ser Ala Pro
            340                 345                 350

His Pro Glu Arg Arg Pro Asn Gly Tyr Ala Leu Gly Leu Val Ser Gly
        355                 360                 365

Gly Ser Ala Gln Glu Ser Gln Gly Asn Thr Gly Leu Pro Asp Val Glu
        370                 375                 380

Leu Leu Ser His Glu Leu Lys Gly Val Cys Pro Glu Pro Pro Gly Leu
385                 390                 395                 400

Asp Asp Pro Leu Ala Gln Asp Gly Ala Gly Val Ser
            405                 410

FIG. 3B

```
         10              30              50
ATGCCCATCA TGGGCTCCTC GGTGTACATC ACGGTGGAGC TGGCCATTGC TGTGCTGGCC
         70              90             110
ATCCTGGGCA ATGTGCTGGT GTGCTGGGCC GTGTGGCTCA ACAGCAACCT GCAGAACGTC
        130             150             170
ACCAACTACT TTGTGGTGTC ACTGGCGGCG GCCGACATCG CAGTGGGTGT GCTCGCCATC
        190             210             230
CCCTTTGCCA TCACCATCAG CACCGGGTTC TGCGCTGCCT GCCACGGCTG CCTCTTCATT
        250             270             290
GCCTGCTTCG TCCTGGTCCT CACGCAGAGC TCCATCTTCA GTCTCCTGGC CATCGCCATT
        310             330             350
GACCGCTACA TTGCCATCCG CATCCCGCTC CGGTACAATG GCTTGGTGAC CGGCACGAGG
        370             390             410
GCTAAGGGCA TCATTGCCAT CTGCTGGGTG CTGTCGTTTG CCATCGGCCT GACTCCCATG
        430             450             470
CTAGGTTGGA ACAACTGCGG TCAGCCAAAG GAGGGCAAGA ACCACTCCCA GGGCTGCGGG
        490             510             530
GAGGGCCAAG TGGCCTGTCT CTTTGAGGAT GTGGTCCCCA TGAACTACAT GGTGTACTTC
        550             570             590
AACTTCTTTG CCTGTGTGCT GGTGCCCCTG CTGCTCATGC TGGGTGTCTA TTTGCGGATC
        610             630             650
TTCCTGGCGG CGCGACGACA GCTGAAGCAG ATGGAGAGCC AGCCTCTGCC GGGGGAGCGG
        670             690             710
GCACGGTCCA CACTGCAGAA GGAGGTCCAT GCTGCCAAGT CACTGGCCAT CATTGTGGGG
        730             750             770
CTCTTTGCCC TCTGCTGGCT GCCCCTACAC ATCATCAACT GCTTCACTTT CTTCTGCCCC
        790             810             830
GACTGCAGCC ACGCCCCTCT CTGGCTCATG TACCTGGCCA TCGTCCTCTC CCACACCAAT
        850             870             890
TCGGTTGTGA ATCCCTTCAT CTACGCCTAC CGTATCCGCG AGTTCCGCCA GACCTTCCGC
        910             930             950
AAGATCATTC GCAGCCACGT CCTGAGGCAG CAAGAACCTT TCAAGGCAGC TGGCACCAGT
        970             990            1010
GCCCGGGTCT TGGCAGCTCA TGGCAGTGAC GGAGAGCAGG TCAGCCTCCG TCTCAACGGC
       1030            1050            1070
CACCCGCCAG GAGTGTGGGC CAACGGCAGT GCTCCCCACC CTGAGCGGAG GCCCAATGGC
       1090            1110            1130
TATGCCCTGG GGCTGGTGAG TGGAGGGAGT GCCCAAGAGT CCCAGGGGAA CACGGGCCTC
       1150            1170            1190
CCAGACGTGG AGCTCCTTAG CCATGAGCTC AAGGGAGTGT GCCCAGAGCC CCCTGGCCTA
       1210            1230
GATGACCCCC TGGCCCAGGA TGGAGCAGGA GTGTCCTGA
```

FIG. 4

| Met | Leu | Leu | Glu | Thr | Gln | Asp | Ala | Leu | Tyr | Val | Ala | Leu | Glu | Leu | Val |
|---|---|---|---|---|---|---|---|---|---|---|---|---|---|---|---|
| 1 | | | | 5 | | | | | 10 | | | | | 15 | |

| Ile | Ala | Ala | Leu | Ser | Val | Ala | Gly | Asn | Val | Leu | Val | Cys | Ala | Ala | Val |
|---|---|---|---|---|---|---|---|---|---|---|---|---|---|---|---|
| | | | | 20 | | | | | 25 | | | | | 30 | |

| Gly | Thr | Ala | Asn | Thr | Leu | Gln | Thr | Pro | Thr | Asn | Tyr | Phe | Leu | Val | Ser |
|---|---|---|---|---|---|---|---|---|---|---|---|---|---|---|---|
| | | | 35 | | | | | 40 | | | | 45 | | | |

| Leu | Ala | Ala | Ala | Asp | Val | Ala | Val | Gly | Leu | Phe | Ala | Ile | Pro | Phe | Ala |
|---|---|---|---|---|---|---|---|---|---|---|---|---|---|---|---|
| | | | 50 | | | | 55 | | | | | 60 | | | |

| Ile | Thr | Ile | Ser | Leu | Gly | Phe | Cys | Thr | Asp | Phe | Tyr | Gly | Cys | Leu | Phe |
|---|---|---|---|---|---|---|---|---|---|---|---|---|---|---|---|
| 65 | | | | | 70 | | | | 75 | | | | | | 80 |

| Leu | Ala | Cys | Phe | Val | Leu | Val | Leu | Thr | Gln | Ser | Ser | Ile | Phe | Ser | Leu |
|---|---|---|---|---|---|---|---|---|---|---|---|---|---|---|---|
| | | | | 85 | | | | | 90 | | | | | 95 | |

| Leu | Ala | Val | Ala | Val | Asp | Arg | Tyr | Leu | Ala | Ile | Cys | Val | Pro | Leu | Arg |
|---|---|---|---|---|---|---|---|---|---|---|---|---|---|---|---|
| | | | | 100 | | | | | 105 | | | | | 110 | |

| Tyr | Lys | Ser | Leu | Val | Thr | Gly | Thr | Arg | Ala | Arg | Gly | Val | Ile | Ala | Val |
|---|---|---|---|---|---|---|---|---|---|---|---|---|---|---|---|
| | | | 115 | | | | | 120 | | | | | 125 | | |

| Leu | Trp | Val | Leu | Ala | Phe | Gly | Ile | Gly | Leu | Thr | Pro | Phe | Leu | Gly | Trp |
|---|---|---|---|---|---|---|---|---|---|---|---|---|---|---|---|
| | | 130 | | | | | 135 | | | | | 140 | | | |

| Asn | Ser | Lys | Asp | Ser | Ala | Thr | Asn | Asn | Cys | Thr | Glu | Pro | Trp | Asp | Gly |
|---|---|---|---|---|---|---|---|---|---|---|---|---|---|---|---|
| 145 | | | | | 150 | | | | | 155 | | | | | 160 |

| Thr | Thr | Asn | Glu | Ser | Cys | Cys | Leu | Val | Lys | Cys | Leu | Phe | Glu | Asn | Val |
|---|---|---|---|---|---|---|---|---|---|---|---|---|---|---|---|
| | | | | 165 | | | | | 170 | | | | | 175 | |

| Val | Pro | Met | Ser | Tyr | Met | Val | Tyr | Phe | Asn | Phe | Phe | Gly | Cys | Val | Leu |
|---|---|---|---|---|---|---|---|---|---|---|---|---|---|---|---|
| | | | 180 | | | | | 185 | | | | | 190 | | |

| Pro | Pro | Leu | Leu | Ile | Met | Leu | Val | Ile | Tyr | Ile | Lys | Ile | Phe | Leu | Val |
|---|---|---|---|---|---|---|---|---|---|---|---|---|---|---|---|
| | | | 195 | | | | 200 | | | | | 205 | | | |

FIG. 5A

Ala Cys Arg Gln Leu Gln Arg Thr Glu Leu Met Asp His Ser Arg Thr
    210                 215                 220

Thr Leu Gln Arg Glu Ile His Ala Ala Lys Ser Leu Ala Met Ile Val
225                 230                 235                 240

Gly Ile Phe Ala Leu Cys Trp Leu Pro Val His Ala Val Asn Cys Val
            245                 250                 255

Thr Leu Phe Gln Pro Ala Gln Gly Lys Asn Lys Pro Lys Trp Ala Met
            260                 265                 270

Asn Met Ala Ile Leu Leu Ser His Ala Asn Ser Val Val Asn Pro Ile
        275                 280                 285

Val Tyr Ala Tyr Arg Asn Arg Asp Phe Arg Tyr Thr Phe His Lys Ile
    290                 295                 300

Ile Ser Arg Tyr Leu Leu Cys Gln Ala Asp Val Lys Ser Gly Asn Gly
305                 310                 315                 320

Gln Ala Gly Val Gln Pro Ala Leu Gly Val Gly Leu
            325                 330

FIG. 5B

```
         10                  30                  50
ATGCTGCTGG AGACACAGGA CGCGCTGTAC GTGGCGCTGG AGCTGGTCAT CGCCGCGCTT
         70                  90                 110
TCGGTGGCGG GCAACGTGCT GGTGTGCGCC GCGGTGGGCA CGGCGAACAC TCTGCAGACG
        130                 150                 170
CCCACCAACT ACTTCCTGGT GTCCCTGGCT GCGGCCGACG TGGCCGTGGG GCTCTTCGCC
        190                 210                 230
ATCCCCTTTG CCATCACCAT CAGCCTGGGC TTCTGCACTG ACTTCTACGG CTGCCTCTTC
        250                 270                 290
CTCGCCTGCT TCGTGCTGGT GCTCACGCAG AGCTCCATCT TCAGCCTTCT GGCCGTGGCA
        310                 330                 350
GTCGACAGAT ACCTGGCCAT CTGTGTCCCG CTCAGGTATA AAGTTTGGT CACGGGGACC
        370                 390                 410
CGAGCAAGAG GGGTCATTGC TGTCCTCTGG GTCCTTGCCT TTGGCATCGG ATTGACTCCA
        430                 450                 470
TTCCTGGGGT GGAACAGTAA AGACAGTGCC ACCAACAACT GCACAGAACC CTGGGATGGA
        490                 510                 530
ACCACGAATG AAAGCTGCTG CCTTGTGAAG TGTCTCTTTG AGAATGTGGT CCCCATGAGC
        550                 570                 590
TACATGGTAT ATTTCAATTT CTTTGGGTGT GTTCTGCCCC CACTGCTTAT AATGCTGGTG
        610                 630                 650
ATCTACATTA AGATCTTCCT GGTGGCCTGC AGGCAGCTTC AGCGCACTGA GCTGATGGAC
        670                 690                 710
CACTCGAGGA CCACCCTCCA GCGGGAGATC CATGCAGCCA AGTCACTGGC CATGATTGTG
        730                 750                 770
GGGATTTTTG CCCTGTGCTG GTTACCTGTG CATGCTGTTA ACTGTGTCAC TCTTTTCCAG
        790                 810                 850
CCAGCTCAGG GTAAAAATAA GCCCAAGTGG GCAATGAATA TGGCCATTCT TCTGTCACAT
        870                 890                 910
GCCAATTCAG TTGTCAATCC CATTGTCTAT GCTTACCGGA ACCGAGACTT CCGCTACACT
        930                 950                 970
TTTCACAAAA TTATCTCCAG GTATCTTCTC TGCCAAGCAG ATGTCAAGAG TGGGAATGGT
        990                1010
CAGGCTGGGG TACAGCCTGC TCTCGGTGTG GGCCTATGA
```

FIG. 6

```
Met Pro Asn Asn Ser Thr Ala Leu Ser Leu Ala Asn Val Thr Tyr Ile
1               5                   10                  15

Thr Met Glu Ile Phe Ile Gly Leu Cys Ala Ile Val Gly Asn Val Leu
            20                  25                  30

Val Ile Cys Val Val Lys Leu Asn Pro Ser Leu Gln Thr Thr Thr Phe
        35                  40                  45

Tyr Phe Ile Val Ser Leu Ala Leu Ala Asp Ile Ala Val Gly Val Leu
        50                  55                  60

Val Met Pro Leu Ala Ile Val Val Ser Leu Gly Ile Thr Ile His Phe
65                  70                  75                  80

Tyr Ser Cys Leu Phe Met Thr Cys Leu Leu Leu Ile Phe Thr His Ala
            85                  90                  95

Ser Ile Met Ser Leu Leu Ala Ile Ala Val Asp Arg Tyr Leu Arg Val
            100                 105                 110

Lys Leu Thr Val Arg Tyr Lys Arg Val Thr Thr His Arg Arg Ile Trp
        115                 120                 125

Leu Ala Leu Gly Leu Cys Trp Leu Val Ser Phe Leu Val Gly Leu Thr
        130                 135                 140

Pro Met Phe Gly Trp Asn Met Lys Leu Thr Ser Glu Tyr His Arg Asn
145                 150                 155                 160

Val Thr Phe Leu Ser Cys Gln Phe Val Ser Val Met Arg Met Asp Tyr
            165                 170                 175

Met Val Tyr Phe Ser Phe Leu Thr Trp Ile Phe Ile Pro Leu Val Val
            180                 185                 190

Met Cys Ala Ile Tyr Leu Asp Ile Phe Tyr Ile Ile Arg Asn Lys Leu
        195                 200                 205

Ser Leu Asn Leu Ser Asn Ser Lys Glu Thr Gly Ala Phe Tyr Gly Arg
        210                 215                 220
```

FIG. 7A

Glu Phe Lys Thr Ala Lys Ser Leu Phe Leu Val Leu Phe Leu Phe Ala
225              230              235              240

Leu Ser Trp Leu Pro Leu Ser Ile Ile Asn Cys Ile Ile Tyr Phe Asn
            245              250              255

Gly Glu Val Pro Gln Leu Val Leu Tyr Met Gly Ile Leu Leu Ser His
            260              265              270

Ala Asn Ser Met Met Asn Pro Ile Val Tyr Ala Tyr Lys Ile Lys Lys
        275              280              285

Phe Lys Glu Thr Tyr Leu Leu Ile Leu Lys Ala Cys Val Val Cys His
    290              295              300

Pro Ser Asp Ser Leu Asp Thr Ser Ile Glu Lys Asn Ser Glu
305              310              315          318

FIG. 7B

```
         10                     30                    50
ATGCCCAACA ACAGCACTGC TCTGTCATTG GCCAATGTTA CCTACATCAC CATGGAAATT
         70                     90                    110
TTCATTGGAC TCTGCGCCAT AGTGGGCAAC GTGCTGGTCA TCTGCGTGGT CAAGCTGAAC
         130                    150                   170
CCCAGCCTGC AGACCACCAC CTTCTATTTC ATTGTCTCTC TAGCCCTGGC TGACATTGCT
         190                    210                   230
GTTGGGGTGC TGGTCATGCC TTTGGCCATT GTTGTCAGCC TGGGCATCAC AATCCACTTC
         250                    270                   290
TACAGCTGCC TTTTTATGAC TTGCCTACTG CTTATCTTTA CCCACGCCTC CATCATGTCC
         310                    330                   350
TTGCTGGCCA TCGCTGTGGA CCGATACTTG CGGGTCAAGC TTACCGTCAG ATACAAGAGG
         370                    390                   410
GTCACCACTC ACAGAAGAAT ATGGCTGGCC CTGGGCCTTT GCTGGCTGGT GTCATTCCTG
         430                    450                   470
GTGGGATTGA CCCCCATGTT TGGCTGGAAC ATGAAACTGA CCTCAGAGTA CCACAGAAAT
         490                    510                   530
GTCACCTTCC TTTCATGCCA ATTTGTTTCC GTCATGAGAA TGGACTACAT GGTATACTTC
         550                    570                   590
AGCTTCCTCA CCTGGATTTT CATCCCCCTG GTTGTCATGT GCGCCATCTA TCTTGACATC
         610                    630                   650
TTTTACATCA TTCGGAACAA ACTCAGTCTG AACTTATCTA ACTCCAAAGA GACAGGTGCA
         670                    690                   710
TTTTATGGAC GGGAGTTCAA GACGGCTAAG TCCTTGTTTC TGGTTCTTTT CTTGTTTGCT
         730                    750                   770
CTGTCATGGC TGCCTTTATC TATCATCAAC TGCATCATCT ACTTTAATGG TGAGGTACCA
         790                    810                   830
CAGCTTGTGC TGTACATGGG CATCCTGCTG TCCCATGCCA ACTCCATGAT GAACCCTATC
         850                    870                   890
GTCTATGCCT ATAAAATAAA GAAGTTCAAG GAAACCTACC TTTTGATCCT CAAAGCCTGT
         910                    930                   950
GTGGTCTGCC ATCCCTCTGA TTCTTTGGAC ACAAGCATTG AGAAGAATTC TGAGTAG
```

FIG. 8

SEQUENCE LISTING ( 1 ) GENERAL INFORMATION:

( i i i ) NUMBER OF SEQUENCES: 28

( 2 ) INFORMATION FOR SEQ ID NO:1:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

ATTCGCAGCC ACGTCCTGAG GCGGCGGGAG CCCTTCAAAG CAGGTGGCAC CAGTGCCCGC 60

( 2 ) INFORMATION FOR SEQ ID NO:2:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

GCGGAGGCTG ATCTGCTCTC CATCACTGCC ATGAGCTGCC AAGGCGCGGG CACTGGTGCC 60

( 2 ) INFORMATION FOR SEQ ID NO:3:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

TCCAGAAGTT CCGGGTCACC TTCCTTAAGA TCTGGAATGA CCACTTCCGC TGCCAGCCCA 60

( 2 ) INFORMATION FOR SEQ ID NO:4:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: cDNA (x i) SEQUENCE DESCRIPTION: SEQ ID NO:4:

AGTCGTGGGG CGCCTCCTCT GGGGGGTCCT CGTCGACGGG GGGCGTGGGC TGGCAGCGGA    60

(2) INFORMATION FOR SEQ ID NO:5:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:5:

GCCTCTTTGA GGATGTGGTC CCCATGAACT ACATGGTGTA CTTCA    45

(2) INFORMATION FOR SEQ ID NO:6:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:6:

GCAGGGGCAC CAGCACACAG GCAAAGAAGT TGAAGTACAC CATGT    45

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:7:

TCGCGCCGCC AGGAAGAT    18

(2) INFORMATION FOR SEQ ID NO:8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:8:

TATATTGAAT TCTAGACACC CAGCATGAGC    30

(2) INFORMATION FOR SEQ ID NO:9:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:9:

TCAATGGCGA TGGCCAGG    18

(2) INFORMATION FOR SEQ ID NO:10:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

TATATTGAAT TCATGGAGCT CTGCGTGAGG        30

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

GTAGACCATG TACTCCAT        18

(2) INFORMATION FOR SEQ ID NO:12:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

TATATTGAAT TCTGACCTTC TCGAACTCGC        30

(2) INFORMATION FOR SEQ ID NO:13:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

ATTGAATTCG ATCACGGGCT CCCCCATGC        29

(2) INFORMATION FOR SEQ ID NO:14:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

ATGGAGTACA TGGTCTACTT CAACTTCTTT GTGTGGGTGC TGCCCCCGCT        50

(2) INFORMATION FOR SEQ ID NO:15:

(i) SEQUENCE CHARACTERISTICS:
        (A) LENGTH: 50 base pairs (B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:15:

GAAGATCCGC AAATAGACAC CCAGCATGAG CAGAAGCGGG GGCAGCACCC     50

(2) INFORMATION FOR SEQ ID NO:16:

(i) SEQUENCE CHARACTERISTICS:
(A) LENGTH: 45 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:16:

CCCTCTAGAG CCCAGCCTGT GCCCGCCATG CCCATCATGG GCTCC     45

(2) INFORMATION FOR SEQ ID NO:17:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:17:

CCCACCTTTT GAGCAAGTTC     20

(2) INFORMATION FOR SEQ ID NO:18:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:18:

GGCTTATGAG TATTTCTTCC     20

(2) INFORMATION FOR SEQ ID NO:19:

(i) SEQUENCE CHARACTERISTICS:
(A) LENGTH: 326 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:19:

| Met | Pro | Pro | Ser | Ile | Ser | Ala | Phe | Gln | Ala | Ala | Tyr | Ile | Gly | Ile | Glu |
| 1 | | | | 5 | | | | | 10 | | | | | 15 | |
| Val | Leu | Ile | Ala | Leu | Val | Ser | Val | Pro | Gly | Asn | Val | Leu | Val | Ile | Trp |
| | | | 20 | | | | | 25 | | | | | 30 | | |
| Ala | Val | Lys | Val | Asn | Gln | Ala | Leu | Arg | Asp | Ala | Thr | Phe | Cys | Phe | Ile |
| | | 35 | | | | | 40 | | | | | 45 | | | |
| Val | Ser | Leu | Ala | Val | Ala | Asp | Val | Ala | Val | Gly | Ala | Leu | Val | Ile | Pro |
| | 50 | | | | | 55 | | | | | 60 | | | | |

| | | | | | | | | | | | | | | | |
|---|---|---|---|---|---|---|---|---|---|---|---|---|---|---|---|
|Leu|Ala|Ile|Leu|Ile|Asn|Ile|Gly|Pro|Gln|Thr|Tyr|Phe|His|Thr|Cys|
|65| | | | |70| | | |75| | | | |80| |
|Leu|Met|Val|Ala|Cys|Pro|Val|Leu|Ile|Leu|Thr|Gln|Ser|Ser|Ile|Leu|
| | | | |85| | | |90| | | | |95| | |
|Ala|Leu|Leu|Ala|Ile|Ala|Val|Asp|Arg|Tyr|Leu|Arg|Val|Lys|Ile|Pro|
| | | |100| | | |105| | | | |110| | | |
|Leu|Arg|Tyr|Lys|Met|Val|Val|Thr|Pro|Arg|Arg|Ala|Ala|Val|Ala|Ile|
| | |115| | | |120| | | | |125| | | | |
|Ala|Gly|Cys|Trp|Ile|Leu|Ser|Phe|Val|Val|Gly|Leu|Thr|Pro|Met|Phe|
| |130| | | |135| | | | |140| | | | | |
|Gly|Trp|Asn|Asn|Leu|Ser|Ala|Val|Glu|Arg|Ala|Trp|Ala|Ala|Asn|Gly|
|145| | | |150| | | | |155| | | | |160| |
|Ser|Met|Gly|Glu|Pro|Val|Ile|Lys|Cys|Glu|Phe|Glu|Lys|Val|Ile|Ser|
| | | |165| | | |170| | | | |175| | | |
|Met|Glu|Tyr|Met|Val|Tyr|Phe|Asn|Phe|Phe|Val|Trp|Val|Leu|Pro|Pro|
| | |180| | | |185| | | | |190| | | | |
|Leu|Leu|Leu|Met|Val|Leu|Ile|Tyr|Leu|Glu|Val|Phe|Tyr|Leu|Ile|Arg|
| | |195| | | |200| | | | |205| | | | |
|Lys|Gln|Leu|Asn|Lys|Lys|Val|Ser|Ala|Ser|Ser|Gly|Asp|Pro|Gln|Lys|
|210| | | |215| | | | |220| | | | | | |
|Tyr|Tyr|Gly|Lys|Glu|Leu|Lys|Ile|Ala|Lys|Ser|Leu|Ala|Leu|Ile|Leu|
|225| | | |230| | | |235| | | | |240| | |
|Phe|Leu|Phe|Ala|Leu|Ser|Trp|Leu|Pro|Leu|His|Ile|Leu|Asn|Cys|Ile|
| | | |245| | | |250| | | | |255| | | |
|Thr|Leu|Phe|Cys|Pro|Ser|Cys|His|Lys|Pro|Ser|Ile|Leu|Thr|Tyr|Ile|
| | |260| | | |265| | | | |270| | | | |
|Ala|Ile|Phe|Leu|Thr|His|Gly|Asn|Ser|Ala|Met|Asn|Pro|Ile|Val|Tyr|
| |275| | | |280| | | | |285| | | | | |
|Ala|Phe|Arg|Ile|Gln|Lys|Phe|Arg|Val|Thr|Phe|Leu|Lys|Ile|Trp|Asn|
|290| | | |295| | | |300| | | | | | | |
|Asp|His|Phe|Arg|Cys|Gln|Pro|Ala|Pro|Pro|Ile|Asp|Glu|Asp|Leu|Pro|
|305| | | |310| | | | |315| | | | |320| |
|Glu|Glu|Arg|Pro|Asp|Asp| | | | | | | | | | |
| | | |325| | | | | | | | | | | | |

( 2 ) INFORMATION FOR SEQ ID NO:20:

( i ) SEQUENCE CHARACTERISTICS:
        ( A ) LENGTH: 981 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:20:

| | | | | | |
|---|---|---|---|---|---|
|ATGCCGCCCT|CCATCTCAGC|TTTCCAGGCC|GCCTACATCG|GCATCGAGGT|GCTCATCGCC|60|
|CTGGTCTCTG|TGCCCGGGAA|CGTGCTGGTG|ATCTGGGCGG|TGAAGGTGAA|CCAGGCGCTG|120|
|CGGGATGCCA|CCTTCTGCTT|CATCGTGTCG|CTGGCGGTGG|CTGATGTGGC|CGTGGGTGCC|180|
|CTGGTCATCC|CCCTCGCCAT|CCTCATCAAC|ATTGGGCCAC|AGACCTACTT|CCACACCTGC|240|
|CTCATGGTTG|CCTGTCCGGT|CCTCATCCTC|ACCCAGAGCT|CCATCCTGGC|CCTGCTGGCA|300|
|ATTGCTGTGG|ACCGCTACCT|CCGGGTCAAG|ATCCCTCTCC|GGTACAAGAT|GGTGGTGACC|360|
|CCCCGGAGGG|CGGCGGTGGC|CATAGCCGGC|TGCTGGATCC|TCTCCTTCGT|GGTGGGACTG|420|
|ACCCCTATGT|TTGGCTGGAA|CAATCTGAGT|GCGGTGGAGC|GGGCCTGGGC|AGCCAACGGC|480|

```
AGCATGGGGG AGCCCGTGAT CAAGTGCGAG TTCGAGAAGG TCATCAGCAT GGAGTACATG      540

GTCTACTTCA ACTTCTTTGT GTGGGTGCTG CCCCCGCTTC TCCTCATGGT CCTCATCTAC      600

CTGGAGGTCT TCTACCTAAT CCGCAAGCAG CTCAACAAGA AGGTGTCGGC CTCCTCCGGC      660

GACCCGCAGA AGTACTATGG GAAGGAGCTG AAGATCGCCA AGTCGCTGGC CCTCATCCTC      720

TTCCTCTTTG CCCTCAGCTG GCTGCCTTTG CACATCCTCA ACTGCATCAC CCTCTTCTGC      780

CCGTCCTGCC ACAAGCCCAG CATCCTTACC TACATTGCCA TCTTCCTCAC GCACGGCAAC      840

TCGGCCATGA ACCCCATTGT CTATGCCTTC CGCATCCAGA AGTTCCGCGT CACCTTCCTT      900

AAGATTTGGA ATGACCATTT CCGCTGCCAG CCTGCACCTC CCATTGACGA GGATCTCCCA      960

GAAGAGAGGC CTGATGACTA G                                                 981
```

(2) INFORMATION FOR SEQ ID NO:21:

(i) SEQUENCE CHARACTERISTICS:
        (A) LENGTH: 412 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:21:

```
Met Pro Ile Met Gly Ser Ser Val Tyr Ile Thr Val Glu Leu Ala Ile
 1               5                  10                  15

Ala Val Leu Ala Ile Leu Gly Asn Val Leu Val Cys Trp Ala Val Trp
                20                  25                  30

Leu Asn Ser Asn Leu Gln Asn Val Thr Asn Tyr Phe Val Val Ser Leu
            35                  40                  45

Ala Ala Ala Asp Ile Ala Val Gly Val Leu Ala Ile Pro Phe Ala Ile
        50                  55                  60

Thr Ile Ser Thr Gly Phe Cys Ala Ala Cys His Gly Cys Leu Phe Ile
 65                  70                  75                  80

Ala Cys Phe Val Leu Val Leu Thr Gln Ser Ser Ile Phe Ser Leu Leu
                85                  90                  95

Ala Ile Ala Ile Asp Arg Tyr Ile Ala Ile Arg Ile Pro Leu Arg Tyr
                100                 105                 110

Asn Gly Leu Val Thr Gly Thr Arg Ala Lys Gly Ile Ile Ala Ile Cys
            115                 120                 125

Trp Val Leu Ser Phe Ala Ile Gly Leu Thr Pro Met Leu Gly Trp Asn
    130                 135                 140

Asn Cys Gly Gln Pro Lys Glu Gly Lys Asn His Ser Gln Gly Cys Gly
145                 150                 155                 160

Glu Gly Gln Val Ala Cys Leu Phe Glu Asp Val Val Pro Met Asn Tyr
                165                 170                 175

Met Val Tyr Phe Asn Phe Phe Ala Cys Val Leu Val Pro Leu Leu Leu
            180                 185                 190

Met Leu Gly Val Tyr Leu Arg Ile Phe Leu Ala Ala Arg Arg Gln Leu
        195                 200                 205

Lys Gln Met Glu Ser Gln Pro Leu Pro Gly Glu Arg Ala Arg Ser Thr
    210                 215                 220

Leu Gln Lys Glu Val His Ala Ala Lys Ser Leu Ala Ile Ile Val Gly
225                 230                 235                 240

Leu Phe Ala Leu Cys Trp Leu Pro Leu His Ile Ile Asn Cys Phe Thr
                245                 250                 255
```

_5,599,671_

31 32

-continued

```
            Phe  Phe  Cys  Pro  Asp  Cys  Ser  His  Ala  Pro  Leu  Trp  Leu  Met  Tyr  Leu
                           260                      265                      270

Ala  Ile  Val  Leu  Ser  His  Thr  Asn  Ser  Val  Val  Asn  Pro  Phe  Ile  Tyr
                      275                      280                      285

Ala  Tyr  Arg  Ile  Arg  Glu  Phe  Arg  Gln  Thr  Phe  Arg  Lys  Ile  Ile  Arg
                 290                      295                      300

Ser  His  Val  Leu  Arg  Gln  Gln  Glu  Pro  Phe  Lys  Ala  Ala  Gly  Thr  Ser
            305                      310                      315                      320

Ala  Arg  Val  Leu  Ala  Ala  His  Gly  Ser  Asp  Gly  Glu  Gln  Val  Ser  Leu
                                325                      330                      335

Arg  Leu  Asn  Gly  His  Pro  Pro  Gly  Val  Trp  Ala  Asn  Gly  Ser  Ala  Pro
                           340                      345                      350

His  Pro  Glu  Arg  Arg  Pro  Asn  Gly  Tyr  Ala  Leu  Gly  Leu  Val  Ser  Gly
                      355                      360                      365

Gly  Ser  Ala  Gln  Glu  Ser  Gln  Gly  Asn  Thr  Gly  Leu  Pro  Asp  Val  Glu
                 370                      375                      380

Leu  Leu  Ser  His  Glu  Leu  Lys  Gly  Val  Cys  Pro  Glu  Pro  Pro  Gly  Leu
            385                      390                      395                      400

Asp  Asp  Pro  Leu  Ala  Gln  Asp  Gly  Ala  Gly  Val  Ser
                                405                      410
```

( 2 ) INFORMATION FOR SEQ ID NO:22:

( i ) SEQUENCE CHARACTERISTICS:
        ( A ) LENGTH: 1239 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:22:

```
ATGCCCATCA  TGGGCTCCTC  GGTGTACATC  ACGGTGGAGC  TGGCCATTGC  TGTGCTGGCC      60
ATCCTGGGCA  ATGTGCTGGT  GTGCTGGGCC  GTGTGGCTCA  ACAGCAACCT  GCAGAACGTC     120
ACCAACTACT  TTGTGGTGTC  ACTGGCGGCG  GCCGACATCG  CAGTGGGTGT  GCTCGCCATC     180
CCCTTTGCCA  TCACCATCAG  CACCGGGTTC  TGCGCTGCCT  GCCACGGCTG  CCTCTTCATT     240
GCCTGCTTCG  TCCTGGTCCT  CACGCAGAGC  TCCATCTTCA  GTCTCCTGGC  CATCGCCATT     300
GACCGCTACA  TTGCCATCCG  CATCCCGCTC  CGGTACAATG  CTTGGTGAC   CGGCACGAGG     360
GCTAAGGGCA  TCATTGCCAT  CTGCTGGGTG  CTGTCGTTTG  CCATCGGCCT  GACTCCCATG     420
CTAGGTTGGA  ACAACTGCGG  TCAGCCAAAG  GAGGGCAAGA  ACCACTCCCA  GGGCTGCGGG     480
GAGGGCCAAG  TGGCCTGTCT  CTTTGAGGAT  GTGGTCCCCA  TGAACTACAT  GGTGTACTTC     540
AACTTCTTTG  CCTGTGTGCT  GGTGCCCCTG  CTGCTCATGC  TGGGTGTCTA  TTTGCGGATC     600
TTCCTGGCGG  CGCGACGACA  GCTGAAGCAG  ATGGAGAGCC  AGCCTCTGCC  GGGGGAGCGG     660
GCACGGTCCA  CACTGCAGAA  GGAGGTCCAT  GCTGCCAAGT  CACTGGCCAT  CATTGTGGGG     720
CTCTTTGCCC  TCTGCTGGCT  GCCCCTACAC  ATCATCAACT  GCTTCACTTT  CTTCTGCCCC     780
GACTGCAGCC  ACGCCCCTCT  CTGGCTCATG  TACCTGGCCA  TCGTCCTCTC  CCACACCAAT     840
TCGGTTGTGA  ATCCCTTCAT  CTACGCCTAC  CGTATCCGCG  AGTTCCGCCA  GACCTTCCGC     900
AAGATCATTC  GCAGCCACGT  CCTGAGGCAG  CAAGAACCTT  TCAAGGCAGC  TGGCACCAGT     960
GCCCGGGTCT  TGGCAGCTCA  TGGCAGTGAC  GGAGAGCAGG  TCAGCCTCCG  TCTCAACGGC    1020
CACCCGCCAG  GAGTGTGGGC  CAACGGCAGT  GCTCCCCACC  CTGAGCGGAG  GCCCAATGGC    1080
TATGCCCTGG  GGCTGGTGAG  TGGAGGGAGT  GCCCAAGAGT  CCCAGGGGAA  CACGGGCCTC    1140
```

```
CCAGACGTGG AGCTCCTTAG CCATGAGCTC AAGGGAGTGT GCCCAGAGCC CCCTGGCCTA      1200

GATGACCCCC TGGCCCAGGA TGGAGCAGGA GTGTCCTGA                             1239
```

( 2 ) INFORMATION FOR SEQ ID NO:23:

( i ) SEQUENCE CHARACTERISTICS:
        ( A ) LENGTH: 332 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:23:

```
Met Leu Leu Glu Thr Gln Asp Ala Leu Tyr Val Ala Leu Glu Leu Val
 1               5                  10                 15

Ile Ala Ala Leu Ser Val Ala Gly Asn Val Leu Val Cys Ala Ala Val
            20                  25                 30

Gly Thr Ala Asn Thr Leu Gln Thr Pro Thr Asn Tyr Phe Leu Val Ser
        35                  40                 45

Leu Ala Ala Ala Asp Val Ala Val Gly Leu Phe Ala Ile Pro Phe Ala
    50                  55                 60

Ile Thr Ile Ser Leu Gly Phe Cys Thr Asp Phe Tyr Gly Cys Leu Phe
65                  70                  75                 80

Leu Ala Cys Phe Val Leu Val Leu Thr Gln Ser Ser Ile Phe Ser Leu
                85                  90                 95

Leu Ala Val Ala Val Asp Arg Tyr Leu Ala Ile Cys Val Pro Leu Arg
            100                 105                110

Tyr Lys Ser Leu Val Thr Gly Thr Arg Ala Arg Gly Val Ile Ala Val
        115                 120                125

Leu Trp Val Leu Ala Phe Gly Ile Gly Leu Thr Pro Phe Leu Gly Trp
    130                 135                140

Asn Ser Lys Asp Ser Ala Thr Asn Asn Cys Thr Glu Pro Trp Asp Gly
145                 150                 155                160

Thr Thr Asn Glu Ser Cys Cys Leu Val Lys Cys Leu Phe Glu Asn Val
                165                 170                175

Val Pro Met Ser Tyr Met Val Tyr Phe Asn Phe Phe Gly Cys Val Leu
            180                 185                190

Pro Pro Leu Leu Ile Met Leu Val Ile Tyr Ile Lys Ile Phe Leu Val
        195                 200                205

Ala Cys Arg Gln Leu Gln Arg Thr Glu Leu Met Asp His Ser Arg Thr
    210                 215                220

Thr Leu Gln Arg Glu Ile His Ala Ala Lys Ser Leu Ala Met Ile Val
225                 230                 235                240

Gly Ile Phe Ala Leu Cys Trp Leu Pro Val His Ala Val Asn Cys Val
                245                 250                255

Thr Leu Phe Gln Pro Ala Gln Gly Lys Asn Lys Pro Lys Trp Ala Met
            260                 265                270

Asn Met Ala Ile Leu Leu Ser His Ala Asn Ser Val Val Asn Pro Ile
        275                 280                285

Val Tyr Ala Tyr Arg Asn Arg Asp Phe Arg Tyr Thr Phe His Lys Ile
    290                 295                300

Ile Ser Arg Tyr Leu Leu Cys Gln Ala Asp Val Lys Ser Gly Asn Gly
305                 310                 315                320

Gln Ala Gly Val Gln Pro Ala Leu Gly Val Gly Leu
                325                 330
```

( 2 ) INFORMATION FOR SEQ ID NO:24:

( i ) SEQUENCE CHARACTERISTICS:
        ( A ) LENGTH: 999 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:24:

| | | | | | | |
|---|---|---|---|---|---|---|
| ATGCTGCTGG | AGACACAGGA | CGCGCTGTAC | GTGGCGCTGG | AGCTGGTCAT | CGCCGCGCTT | 60 |
| TCGGTGGCGG | GCAACGTGCT | GGTGTGCGCC | GCGGTGGGCA | CGGCGAACAC | TCTGCAGACG | 120 |
| CCCACCAACT | ACTTCCTGGT | GTCCCTGGCT | GCGGCCGACG | TGGCCGTGGG | GCTCTTCGCC | 180 |
| ATCCCCTTTG | CCATCACCAT | CAGCCTGGGC | TTCTGCACTG | ACTTCTACGG | CTGCCTCTTC | 240 |
| CTCGCCTGCT | TCGTGCTGGT | GCTCACGCAG | AGCTCCATCT | TCAGCCTTCT | GGCCGTGGCA | 300 |
| GTCGACAGAT | ACCTGGCCAT | CTGTGTCCCG | CTCAGGTATA | AAGTTTGGT | CACGGGGACC | 360 |
| CGAGCAAGAG | GGGTCATTGC | TGTCCTCTGG | GTCCTTGCCT | TTGGCATCGG | ATTGACTCCA | 420 |
| TTCCTGGGGT | GGAACAGTAA | AGACAGTGCC | ACCAACAACT | GCACAGAACC | CTGGGATGGA | 480 |
| ACCACGAATG | AAAGCTGCTG | CCTTGTGAAG | TGTCTCTTTG | AGAATGTGGT | CCCCATGAGC | 540 |
| TACATGGTAT | ATTTCAATTT | CTTTGGGTGT | GTTCTGCCCC | CACTGCTTAT | AATGCTGGTG | 600 |
| ATCTACATTA | AGATCTTCCT | GGTGGCCTGC | AGGCAGCTTC | AGCGCACTGA | GCTGATGGAC | 660 |
| CACTCGAGGA | CCACCCTCCA | GCGGGAGATC | CATGCAGCCA | AGTCACTGGC | CATGATTGTG | 720 |
| GGGATTTTTG | CCCTGTGCTG | GTTACCTGTG | CATGCTGTTA | ACTGTGTCAC | TCTTTTCCAG | 780 |
| CCAGCTCAGG | GTAAAAATAA | GCCCAAGTGG | GCAATGAATA | TGGCCATTCT | TCTGTCACAT | 840 |
| GCCAATTCAG | TTGTCAATCC | CATTGTCTAT | GCTTACCGGA | ACCGAGACTT | CCGCTACACT | 900 |
| TTTCACAAAA | TTATCTCCAG | GTATCTTCTC | TGCCAAGCAG | ATGTCAAGAG | TGGGAATGGT | 960 |
| CAGGCTGGGG | TACAGCCTGC | TCTCGGTGTG | GGCCTATGA | | | 999 |

( 2 ) INFORMATION FOR SEQ ID NO:25:

( i ) SEQUENCE CHARACTERISTICS:
        ( A ) LENGTH: 318 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:25:

| | | | | | | | | | | | | | | |
|---|---|---|---|---|---|---|---|---|---|---|---|---|---|---|
| Met | Pro | Asn | Asn | Ser | Thr | Ala | Leu | Ser | Leu | Ala | Asn | Val | Thr | Tyr | Ile |
| 1 | | | | 5 | | | | | 10 | | | | | 15 | |
| Thr | Met | Glu | Ile | Phe | Ile | Gly | Leu | Cys | Ala | Ile | Val | Gly | Asn | Val | Leu |
| | | | 20 | | | | | 25 | | | | | 30 | | |
| Val | Ile | Cys | Val | Val | Lys | Leu | Asn | Pro | Ser | Leu | Gln | Thr | Thr | Thr | Phe |
| | | 35 | | | | | 40 | | | | | 45 | | | |
| Tyr | Phe | Ile | Val | Ser | Leu | Ala | Leu | Ala | Asp | Ile | Ala | Val | Gly | Val | Leu |
| | 50 | | | | | 55 | | | | | 60 | | | | |
| Val | Met | Pro | Leu | Ala | Ile | Val | Val | Ser | Leu | Gly | Ile | Thr | Ile | His | Phe |
| 65 | | | | | 70 | | | | | 75 | | | | | 80 |
| Tyr | Ser | Cys | Leu | Phe | Met | Thr | Cys | Leu | Leu | Leu | Ile | Phe | Thr | His | Ala |
| | | | | 85 | | | | | 90 | | | | | 95 | |

|   |   |   |   |   |   |   |   |   |   |   |   |   |   |   |
|---|---|---|---|---|---|---|---|---|---|---|---|---|---|---|
| Ser | Ile | Met | Ser 100 | Leu | Leu | Ala | Ile 105 | Ala | Val | Asp | Arg | Tyr | Leu 110 | Arg Val |
| Lys | Leu | Thr 115 | Val | Arg | Tyr | Lys | Arg 120 | Val | Thr | Thr | His | Arg 125 | Arg | Ile Trp |
| Leu | Ala 130 | Leu | Gly | Leu | Cys | Trp 135 | Leu | Val | Ser | Phe | Leu 140 | Val | Gly | Leu Thr |
| Pro 145 | Met | Phe | Gly | Trp | Asn 150 | Met | Lys | Leu | Thr | Ser 155 | Glu | Tyr | His | Arg Asn 160 |
| Val | Thr | Phe | Leu | Ser 165 | Cys | Gln | Phe | Val | Ser 170 | Val | Met | Arg | Met | Asp Tyr 175 |
| Met | Val | Tyr | Phe 180 | Ser | Phe | Leu | Thr | Trp 185 | Ile | Phe | Ile | Pro | Leu 190 | Val Val |
| Met | Cys | Ala 195 | Ile | Tyr | Leu | Asp | Ile 200 | Phe | Tyr | Ile | Ile | Arg 205 | Asn | Lys Leu |
| Ser | Leu 210 | Asn | Leu | Ser | Asn | Ser 215 | Lys | Glu | Thr | Gly | Ala 220 | Phe | Tyr | Gly Arg |
| Glu 225 | Phe | Lys | Thr | Ala | Lys 230 | Ser | Leu | Phe | Leu | Val 235 | Leu | Phe | Leu | Phe Ala 240 |
| Leu | Ser | Trp | Leu | Pro 245 | Leu | Ser | Ile | Ile | Asn 250 | Cys | Ile | Ile | Tyr | Phe Asn 255 |
| Gly | Glu | Val | Pro 260 | Gln | Leu | Val | Leu | Tyr 265 | Met | Gly | Ile | Leu | Leu 270 | Ser His |
| Ala | Asn | Ser 275 | Met | Met | Asn | Pro | Ile 280 | Val | Tyr | Ala | Tyr | Lys 285 | Ile | Lys Lys |
| Phe | Lys 290 | Glu | Thr | Tyr | Leu | Leu 295 | Ile | Leu | Lys | Ala | Cys 300 | Val | Val | Cys His |
| Pro 305 | Ser | Asp | Ser | Leu | Asp 310 | Thr | Ser | Ile | Glu | Lys 315 | Asn | Ser | Glu 318 |  |

( 2 ) INFORMATION FOR SEQ ID NO:26:

( i ) SEQUENCE CHARACTERISTICS:
( A ) LENGTH: 957 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:26:

| | | | | | |
|---|---|---|---|---|---|
| ATGCCCAACA | ACAGCACTGC | TCTGTCATTG | GCCAATGTTA | CCTACATCAC | CATGGAAATT | 60 |
| TTCATTGGAC | TCTGCGCCAT | AGTGGGCAAC | GTGCTGGTCA | TCTGCGTGGT | CAAGCTGAAC | 120 |
| CCCAGCCTGC | AGACCACCAC | CTTCTATTTC | ATTGTCTCTC | TAGCCCTGGC | TGACATTGCT | 180 |
| GTTGGGGTGC | TGGTCATGCC | TTTGGCCATT | GTTGTCAGCC | TGGGCATCAC | AATCCACTTC | 240 |
| TACAGCTGCC | TTTTTATGAC | TTGCCTACTG | CTTATCTTTA | CCCACGCCTC | CATCATGTCC | 300 |
| TTGCTGGCCA | TCGCTGTGGA | CCGATACTTG | CGGGTCAAGC | TTACCGTCAG | ATACAAGAGG | 360 |
| GTCACCACTC | ACAGAAGAAT | ATGGCTGGCC | CTGGGCCTTT | GCTGGCTGGT | GTCATTCCTG | 420 |
| GTGGGATTGA | CCCCCATGTT | TGGCTGGAAC | ATGAAACTGA | CCTCAGAGTA | CCACAGAAAT | 480 |
| GTCACCTTCC | TTTCATGCCA | ATTTGTTTCC | GTCATGAGAA | TGGACTACAT | GGTATACTTC | 540 |
| AGCTTCCTCA | CCTGGATTTT | CATCCCCCTG | GTTGTCATGT | GCGCCATCTA | TCTTGACATC | 600 |
| TTTTACATCA | TTCGGAACAA | ACTCAGTCTG | AACTATCTA | ACTCCAAAGA | GACAGGTGCA | 660 |
| TTTTATGGAC | GGGAGTTCAA | GACGGCTAAG | TCCTTGTTTC | TGGTTCTTTT | CTTGTTTGCT | 720 |
| CTGTCATGGC | TGCCTTTATC | TATCATCAAC | TGCATCATCT | ACTTTAATGG | TGAGGTACCA | 780 |

| | | | | | | |
|---|---|---|---|---|---|---|
| CAGCTTGTGC | TGTACATGGG | CATCCTGCTG | TCCCATGCCA | ACTCCATGAT | GAACCCTATC | 840 |
| GTCTATGCCT | ATAAAATAAA | GAAGTTCAAG | GAAACCTACC | TTTTGATCCT | CAAAGCCTGT | 900 |
| GTGGTCTGCC | ATCCCTCTGA | TTCTTTGGAC | ACAAGCATTG | AGAAGAATTC | TGAGTAG | 957 |

(2) INFORMATION FOR SEQ ID NO:27:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

| | | | |
|---|---|---|---|
| CCCAAGCTTA | TGAAAGCCAA | CAATACC | 27 |

(2) INFORMATION FOR SEQ ID NO:28:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:28:

| | | | |
|---|---|---|---|
| TGCTCTAGAC | TCTGGTATCT | TCACATT | 27 |

HUMAN A2B ADENOSINE RECEPTOR ASSAY

This application is a continuation of application Ser. No. 08/005,945, filed on Jan. 15 1993, now abandoned, which is a continuation-in-part of application Ser. No. 07/850,702, filed Mar. 13, 1992, now abandoned, application Ser. No. 07/850,701, filed Mar. 13, 1992, now abandoned, and application Ser. No. 07/850,707, filed Mar. 13, 1992, now abandoned.

BACKGROUND OF THE INVENTION

The present invention concerns cloned human adenosine receptors of the A1, A2 and A3 class and their subtypes. The cloned dog A1 and A2a adenosine receptors have been reported. See F. Libert, et al., (1989) Science 244:569–572, C. Maennant, et al., Biochem. Biophys. Res. Comm., (1990) 173:1169–1178, and F. Libert, et al. (1991) EMBO J. 10:1677–1682. The cloned rat A1 adenosine receptor has been reported by L. C. Mahan, et al., (1991) Mol. Pharm. 40:1–7 and S. M. Reppert, et al., (1991) Mol. Endocrin. 5:1037–1048. We have now found that the human A1 adenosine receptor differs by 18 amino acids from the dog A1 sequence and 16 amino acids from the rat A1 sequence. The human A2a adenosine receptor differs by 28 amino acids from the dog A2a sequence.

Adenosine is a naturally occurring nucleoside which exhibits diverse and potent physiological actions in the cardiovascular, nervous, pulmonary, renal and immune systems. Adenosine has been demonstrated to terminate supraventricular tachycardia through blockage of atrioventricular nodal conduction (J. P. DiMarco, et al., (1985) J. Am. Col. Cardiol. 6:417–425, A. Munoz, et al., (1984) Eur. Heart J. 5:735–738). Adenosine is a potent vasodilator except in the kidney and placenta (R. A. Olsson, (1981) Ann. Rev. Physiol. 43:385–395). Adenosine has been implicated as a preventative agent and in treatment of ventricular dysfunction following episodes of regional or global ischemia (M. B. Forman and C. E. Velasco (1991) Cardiovasc. Drugs and Therapy 5:901–908) and in cerebral ischemia(M. C. Evans, et al., (1987) Neurosci. Lett. 83:287, D. K. J. E., Von Lubitz, et al., (1988) Stroke 19:1133).

The instant invention also concerns an assay protocol which can be used for identifying and evaluating substances that bind to human adenosine receptors. The assay can be utilized to identify adenosine receptor agonists and antagonists and determine their binding affinity (R. F. Bruns, et al., (1983) Proc. Natl. Acad. Sci. USA 80:2077–2080; R. F. Bruns, et al.,(1986) Mol. Pharmacol. 29:331–346; M. F. Jarvis, et al. (1989) J. Pharma. Exp. Therap. 251:888–893; K. A. Jacobson et al., (1989) J. Med. Chem. 32:1043–1051). Such adenosine receptor agonists, antagonists and binding enhancers have been identified and implicated for usage in the treatment of physiological complications resulting from cardiovascular, renal and neurological disorders. Adenosine receptor agonists have been identified for use as vasodilators ((1989) FASEB. J. 3(4) Abs 4770 and 4773, (19910 J. Med. Chem. (1988) 34:2570), antihypertensive agents (D. G. Taylor et al., FASEB J. (1988) 2:1799),and anti-psychotic agents (T. G. Heffner et al., (1989) Psychopharmacology 98:31–38). Adenosine receptor agonists have been identified for use in improving renal function (R. D. Murray and P. C. Churchill,(1985) J. Pharmacol. Exp. Therap. 232:189–193) Adenosine receptor allosteric or binding enhancers have shown utility in the treatment of ischemia, seizures or hypoxia of the brain (R. F. Bruns, et al. (1990) Mol. Pharmacol. 38:939–949; C. A. Janusz, et al., (1991) Brain Research 567:181–187). The cardioprotective agent, 5-amino-4imidazole carboxamide (AICA) ribose has utility in the treatment of ischemic heart conditions, including unstable angina and acute s myocardial infarction (H. E. Gruber, et al. (1989) Circulation 80: 1400–1414). Previous methods to date have proven inferior due to the presence of multiple subtypes present in the animal tissue utilized (R. F. Bruns et al., (1986) Mol. Pharm. 29:33 1–346) and the differences between species in the affinity for adenosine analogs and the physiological effects of adenosine (Ukera, et al., (1986) FEBS Lett, 209:122–128). Pure adenosine receptors make possible the identification and evaluation of compounds which have unique affinity for a single receptor subtype. Moreover, because of the variable effects of adenosine documented in other species, the utilization of human adenosine receptor subtypes is advantageous for the development of human therapeutic adenosine receptor agonists, antagonists or enhancers.

BRIEF DESCRIPTION OF THE DRAWINGS

FIGS. 1A and 1B Full length amino acid sequence of human A1 adenosine receptor.

FIG. 2 Full length nucleotide sequence of the cloned human A1 adenosine receptor complementary DNA depicted from the 5' to 3' terminus.

FIGS. 3A and 3B Full length amino acid sequence of human A2a adenosine receptor.

FIG. 4 Full length nucleotide sequence of cloned human A2a adenosine receptor complementary DNA depicted from the 5' to 3' terminus.

FIGS. 5A and 5B Full length amino acid sequence of human A2b receptor.

FIG. 6 Full length nucleotide sequence of cloned human A2b adenosine receptor complementary DNA depicted from the 5' to 3' terminus.

FIGS. 7A and 7B Full length amino acid sequence of human A3 adenosine receptor.

FIG. 8 Full length nucleotide sequence of the cloned human A3 adenosine receptor complementary DNA depicted from the 5' to 3' terminus.

SUMMARY OF THE INVENTION

The invention concerns recombinant human adenosine receptors A1, A2a, A2b and A3, which have been prepared by cDNA cloning and polymerase chain reaction techniques. The invention also concerns expression systems for these receptors in COS cells, CHO cells and/or oocytes, as well as an assay using the expression system.

The recombinant adenosine receptors comprising the invention can be utilized in an assay to identify and evaluate entities that bind to or enhance binding to purified human adenosine receptors.

| ABBREVIATIONS | |
| --- | --- |
| Ligands | |
| [$^{125}$I]-ABA | [$^{125}$I]-N$^6$-aminobenzyladenosine |
| [$^{125}$I]-APNEA | [$^{125}$I]-N$^6$-2-(4-amino-3-iodo-phenyl)-ethyl adenosine |
| [$^3$H]-CHA | [$^3$H]-cyclohexyladenosine |
| [$^3$H]-CGS21680 | [$^3$H]-2-[4-(2-carboxyethyl)phen-ethylamino]-5'-N-ethylcarbox-amido-adenosine |

| ABBREVIATIONS | |
|---|---|
| Ligands | |
| [³H]-DPCPX | [³H]-1,3-dipropyl-3-cyclopentylxanthrine |
| [³H]-NECA | [³H]-5'-ethyl-carboxamido-adenosine |

DETAILED DESCRIPTION OF THE INVENTION

One embodiment of the invention concerns human A1 adenosine receptor, said receptor being free of other human receptor proteins.

Within this class, this embodiment concerns human A1 adenosine receptor from human tissue such as brain, kidney or heart, said receptor being free of other human proteins.

In a second class this embodiment concerns a protein comprising the amino acid sequence Leu-Thr-Gln-Ser-Ser (LTQSS) which is amino acids 90 to 94 in FIG. 1A. This sequence is also found in FIG. 3A, amino acids 87 to 91 and FIG. 5A, amino acids 88 to 92.

In a third class, this embodiment concerns a protein comprising the 326 amino acid sequence depicted in FIGS. 1A and 1B said protein being free of other human receptor proteins.

Within the third class this embodiment concerns a protein consisting of the 326 amino acid sequence as shown in FIGS. 1A and 1B.

This embodiment also concerns a cDNA sequence encoding human A1 adenosine receptor, said sequence being free of other human DNA sequences.

Within this aspect, the invention concerns the 981 nucleotide sequence of complementary DNA, as shown in FIG. 2 or a degenerate variation thereof.

A second embodiment concerns human A2a adenosine receptor, said receptor being free of other human receptor proteins.

Within this class, this embodiment concerns human A2a adenosine receptor from human tissue such as brain, kidney or heart, said receptor being free of other human proteins.

In a second class, this embodiment concerns a protein comprising the 412 amino acid sequence depicted in FIGS. 3A and 3B, said protein being free of other human receptor proteins.

Within the third class this embodiment concerns a protein consisting of the 412 amino acid sequence as shown in FIGS. 3A and 3B.

The second embodiment also concerns a complementary DNA sequence encoding human A2a adenosine receptor, said sequence being free of other human DNA sequences.

One class of the second embodiment the invention concerns the 1239 nucleotide sequence of complementary DNA, as shown in FIG. 4 or a degenerate variation thereof.

A third embodiment concerns human A2b adenosine receptor, said receptor being free of other human receptor proteins.

In one class this embodiment concerns human A2b adenosine receptor, said receptor being free of other human proteins.

Within this class, this embodiment concerns human A2b adenosine receptor from human tissue such as brain, said receptor being free of other human proteins.

In a second class, this embodiment concerns a protein comprising the 332 amino acid sequence depicted in FIGS. 5A and 5B, said protein being free of other human receptor proteins.

Within the third class this embodiment concerns a protein consisting of the 332 amino acid sequence as shown in FIGS. 5A and 5B.

The third embodiment also concerns a complementary DNA sequence encoding human A2b adenosine receptor, said sequence being free of other human DNA sequences.

One class of the third embodiment of the invention concerns the 999 nucleotide sequence of complementary DNA, as shown in FIG. 6 or a degenerate variation thereof.

A fourth embodiment concerns human A3 adenosine receptor, said receptor being free of other human receptor proteins.

In one class this embodiment concerns human A3 adenosine receptor, said receptor being free of other human proteins.

Within this class, this embodiment concerns human A3 adenosine receptor from human tissue such as brain, said receptor being free of other human proteins.

In a second class, this embodiment concerns a protein comprising the 3 18 amino acid sequence depicted in FIGS. 7A and 7B, said protein being free of other human receptor proteins.

Within the third class this embodiment concerns a protein consisting of the 318 amino acid sequence as shown in FIGS. 7A and 7B.

The fourth embodiment also concerns a complementary DNA sequence encoding human A3 adenosine receptor, said sequence being free of other human DNA sequences.

One class of the fourth embodiment of the invention concerns the 957 nucleotide sequence of complementary DNA, as shown in FIG. 8 or a degenerate variation thereof.

A fifth embodiment of this invention concerns systems for expressing human A1, A2a, A2b, or A3 adenosine receptor.

In one class this fifth embodiment of the invention comprises:

A plasmid which comprises:
(a) a mammalian expression vector, such as pSVL, and
(b) a nucleotide sequence encoding human A 1, A2a, A2b or A3 adenosine receptor protein.

A second class of this embodiment of the invention concerns a system for the expression of human A 1, A2a, A2b, or A3 adenosine receptor in a mammalian cell line (COS7 or CHO), or in oocytes.

A sixth embodiment of the invention concerns a method of using any of the above expression systems for determining the binding affinity of a test sample for human A 1, A2a, A2b, or A3 adenosine receptor respectively.

In one class this embodiment concerns an adenosine receptor binding assay for a test sample using a mammalian cell line, said mammalian cell line transfected with a plasmid, which plasmid comprises
(a) a mammalian expression vector, and
(b) the nucleotide sequence encoding a human adenosine receptor protein, the assay comprising the steps of:
(1) expressing said human adenosine receptor in a transfected cell line, selected from COS7 cells transfected with said plasmid or CHO cells transfected with said plasmid;
(2) in a solution, mixing a test sample with said transfected cell line and a radioactive ligand;

(3) incubating the mixture of Step 2;
(4) separating said radioactive ligand bound to said human adenosine receptor protein from unbound radioactive ligand; and
(5) measuring the radioactivity of said radioactive ligand bound to said human adenosine receptor;

said human adenosine receptor protein selected from the group comprising A 1, A2a, A2b or A3 human adenosine receptor protein.

There is a variety of ligands useful for characterizing the binding affinity of a given adenosine subtype. The following Table L is illustrative.

TABLE L

| Adenosine Receptor | Preferred Ligands |
|---|---|
| A1 | [$^3$H]-CHA, [$^3$H]-NECA, [$^3$H]-DPCPX |
| A2a | [$^3$H]-GGS21680, [$^3$H]-NECA |
| A2b | [3H]-NECA |
| A3 | [$^{125}$I]-ABA, [$^{125}$I]-APNEA, [$^3$H]-NECA |

It will be a readily apparent to the skilled artisan that other ligands may be useful in adenosine receptor binding assays, including those listed in Table L but with a different radioactive label, and others. Testing of other ligands for high affinity binding is readily performed with the purified adenosine receptor subtypes described in the present invention.

As will be appreciated by those of skill in the art, there is a substantial amount of redundancy in the set of codons which translate specific amino acids. Accordingly, the invention also includes alternative base sequences wherein a codon (or codons) are replaced s with another codon, such that the amino acid sequence translated by the DNA sequence remains unchanged. For purposes of this specification, a sequence bearing one or more such replaced codons will be defined as a degenetate variation. Also included are mutations (exchange of individual amino acids) which one of skill in the art would expect to have no effect on functionality, such as valine for leucine, arginine for lysine and asparagine for glutamine. For purposes of this specification, amino acid sequences beating one or more of such mutations are used to substantially correspond to the sequence defined in FIGS. 1A and 1B, 3A and 3B, 4, 5A and 5B, 7A and 7B, respectively.

In overview, the present specification describes methods by which applicants have isolated human A1, A2a, A2b or A3 adenosine receptor complementary DNA (cDNA) without prior knowledge of its protein sequence or gene sequence. The human A1 and A2a cDNAs were obtained in part from a human heart cDNA library. In the approach, the regions of dog A1 and A2a adenosine receptors were selected by the applicants which they believed to be similar to the human A1 and A2a adenosine receptors. Oligonucleotide probes corresponding to these regions were designed and utilized to obtain part of the human A1 and A2a adenosine receptor cDNA sequence from a human heart cDNA library. The remaining parts of the human heart A1 and A2a adenosine receptor cDNAs were obtained by polymerase chain reaction (PCR) technique utilizing the above sequence information of human A1 and A2a adenosine receptor cDNA. The human A1 and A2a adenosine receptor cDNAs were also isolated from human brain and human kidney cDNA libraries utilizing the above sequence information of human A1 and A2a adenosine receptor cDNAs obtained from the human heart cDNA library. The A2b adenosine receptor subtype cDNA was obtained from a human cortex cDNA library utilizing the above sequence information of human adenosine receptor cDNA. The human A3 was isolated from human striata cDNA library, using a rat A3 fragment obtained by the polymerase chain reaction.

The complete sequence of the human A1, A2a, A2b and A3 adenosine receptor subtype was determined and their protein sequence deduced.

The cloned human adenosine receptor cDNAs were expressed in a heterologous expression system. Expression in COS cells (a monkey kidney cell line) was used to measure ligand binding properties of the human adenosine receptors. Such an expression system can be used for evaluation and identification of adenosine receptor agonists, antagonists or enhancers.

1) Isolation of human adenosine receptor cDNA

To isolate the human A1 and A2a adenosine receptor cDNAs in the absence of its sequence information, a human ventricle cDNA library was screened with oligonucleotide probes based on the published sequence of the dog A1 and A2a adenosine receptor cDNAs (F. Libert, et al., (1989) Science 244:569–572). Partial cDNA sequence was obtained for the human A1 and A2a adenosine receptor cDNAs. The remaining parts of the human A1 and A2a adenosine receptor cDNAs were obtained by PCR using a modification of the method described by Froham et al. ((1988), Proc. Natl. Acad. Sci., 85:8998–9002). PCR primers corresponding to human sequence obtained from the partial human ventricular A1 and A2a adenosine receptor cDNAs were designed and used in PCR amplification of human ventricular mRNA.

The human A1 and A2a adenosine receptors were also isolated from human brain and kidney cDNA libraries. Human oligonucleotide probes were designed based on the human ventricular A1 and A2a adenosine receptor cDNA sequence. The sequence of the brain and kidney A1 adenosine receptor cDNA was identical to the human ventricular A1 adenosine receptor cDNA obtained in part from the human ventricle cDNA library and by PCR methodology.

The human A2b adenosine receptor subtype was obtained from a human cortex cDNA library using human oligonucleotide primers corresponding to a region of the human adenosine receptor cDNA sequence.

The human A3 adenosine receptor subtype was obtained from a striata library using a rat cDNA probe generated by the polymerase chain reaction. Oligonucleotides were designed based on the rat A3 sequence (Zhou et al, Proc. Natl. Acad. Sci.89, 7432(1992)).

2) Expression of the cloned human adenosine receptors

The human A1, A2a, A2b and A3 receptor subtype cDNAs were subcloned into the expression vector pSVL (PHARMACIA). Transient expression in COS7 cells (monkey kidney cell line, ATCC CRL 1651, ATCC, Rockville, Md.) was accomplished by transfection of the cloned adenosine receptor cDNAs under the control of the SV40 promoter into mammalian cells (e.g., COS7). Membranes prepared from the transfected cells were utilized for the determination of binding affinity, selectivity and specificity of the human adenosine receptors for various ligands. Stable expression of the human adenosine receptors in mammalian cells (e.g., COS7 and CHO) was achieved after integration of the transfected cDNA into the chromosomes of the host cells. These stable cell lines constituently express the cloned human adenosine receptors and can be propagated infinitely. Stable cell lines expressing the human adenosine subtype cDNAs individually can be used in the binding assay to measure the affinity and selectivity of the receptors for adenosine agonists, antagonists and enhancers.

Membranes prepared from transfected COS7 cells were utilized in a binding assay to measure the affinity of the human adenosine receptors for the radiolabeled adenosine agonists, [$^3$H]-cyclohexyladenosine (CHA), [$^3$H]-CGS21680 (2-(p-(2-carboxyethyl)-phenylamino)-5'-N-ethyl-carboxamidoadenosine), [$^3$H]-5'-N-ethylcarboxamido adenosine ([³H]-NECA), or [¹²⁵I]-N⁶-aminobenzyl adenosine (¹²⁵I-ABA). Monolayer cell culture of transfected COS7 cells were dissociated with 1 mM EDTA in phosphate buffered saline and resuspended in 5 mM Tris, pH7.6/10 mM MgCl₂. The cells were subjected to freeze-thaw lysis and the suspension was homogenized in a glass dounce homogenizer. The membranes were pelleted, resuspended in binding buffer, 50 mM Tris pH 7.6/10 mM MgCl₂ and incubated with adenosine deaminase before the binding assay. The binding assay was performed by incubating 100 mg of membranes with increasing concentrations of radiolabeled adenosine agonists. Bound ligand was separated from free ligand by filtration on a SKATRON CELL HARVESTER equipped with a receptor binding filtermat. Bound radioactivity was measured by scintillation counting. Substances which bind to or enhance binding to expressed human adenosine receptors in COS and CHO cells can be identified in competition binding assays with radiolabeled adenosine analogs. For the competition binding assay, membranes were incubated with 5 nM [³H]-CHA 5 nM [³H]-CGS21680 or 10 Nm [³H]-NECA and various concentrations of adenosine agonists or antagonists.

A transient expression system in Xenopus oocytes was established by microinjection of in vitro transcribed mRNA from the cloned adenosine receptor cDNAs. The expression system allows the measurement of the biological effects (i.e., changes in cAMP levels) upon activation of the expressed adenosine receptors with ligand binding. The cAMP levels are measured by a radioimmunoassay (RIANEN kit, DuPont/NEN) using the acetylation protocol. Activation of the expressed receptors by ligand binding are coupled to either increases or decreases in the intracellular cAMP levels dependent upon the subtype of adenosine receptor (Van Calker et al., I(1979) J. Neurochem. 33:999–1003; Londos et al. (1980) Proc. Natl. Acad. Sci. USA 77:2551–2554). The activity of any potential adenosine receptor agonist can be evaluated by measuring the changes in cAMP levels in oocytes injected with adenosine receptor mRNA but not in uninjected or negative control injected oocytes. The activity of any potential adenosine receptor antagonist can be evaluated by determining the inhibition of the cAMP response induced by adenosine in oocytes injected with adenosine receptor transcripts but not negative control or uninjected oocytes. The changes in cAMP accumulation can alternatively be measured in stably transfected CHO cells expressing the human adenosine receptor subtypes.

The cAMP accumulation assay has a number of advantages over the binding assay established in the mammalian cell expression system as a screen for adenosine receptor modulating agents. The assay allows the measurement of a biological effect (i.e., changes in cAMP levels) resulting from the activation of the expressed receptors by ligand binding. The native agonist adenosine is utilized in the assay to activate the expressed receptors. The functionality of additional adenosine receptor subtypes identified by molecular cloning which may not have defined ligands for binding analysis can be evaluated with the natural agonist and without prior identification of a selective, high affinity, radiolabeled ligand.

EXAMPLE 1

STEP A:

In the first step of obtaining the partial cDNAs encoding the human A1 and A2a adenosine receptors, total RNA was extracted by homogenizing 2.3 g human ventricle in 20 ml 5M guanidine isothiocyanate, 0.1M sodium citrate, pH 6.3, 1 mM EDTA, pH 7.0, 5% beta-mercaptoethanol, and 0.5% sodium lauryl sarcosinate. The homogenate was centrifuged for 10 min. at 10,000 rpm and the resulting supernatant was layered onto a cushion of 5.7M CsCl/0.1M EDTA, pH 7.0. After 20 hrs. of centrifugation at 24,000 rpm, the resulting pellet was precipitated one time and then passed over an oligo(dT)-cellulose (PHARMACIA, Piscataway, N.J.) column to isolate poly(A)+RNA.

An oligo(dT) primed library was synthesized from 5 µg of the poly(A)⁺ human ventricle RNA using the YOU-PRIME cDNA SYNTHESIS KIT (PHARMACIA, Piscataway, N.J.). See Gubler and Hoffman Gene 25:263 (1983). The resulting double-stranded cDNA was ligated into λgt10 EcoRI arms (PROMEGA, Madison, Wis.) and packaged according to the GIGAPACK II GOLD PACKAGING EXTRACT protocol (STRATAGENE, La Jolla, Calif.). See Huynh et al. (1985) *DNA Cloning Techniques: A Practical Approach*, IRL Press, Oxford, p.49 and Kretz et al. Res. 17:5409.

The *E. coli* strain C600Hfl (PROMEGA, Madison, Wis.) was infected with library phage, plated on agar plates, and incubated at 37° C. The phage DNA was transferred to HYBOND-N nylon membranes (AMERSHAM, Arlington Heights, Ill.) according to the manufacturer's specifications.

Synthetic probes were constructed from overlapping oligonucleotides (A1 probe: 62+63, A2 probe: 52+53; see Table I for their sequences) based on the published dog A1 (RDC7) and A2a(RDC8) sequences (F Libert, et al,(1989) Science 244:569–572). The oligonucleotides were annealed and filled-in with $\alpha^{32}$P-dCTP (NEN, Wilmington, Del.) and Klenow enzyme. The filters were hybridized with the appropriate probe in 5×SSC, 30% formamide, 5×Denhardt's solution, 0.1% SDS, and 0.1mg/ml sonicated salmon sperm DNA at 42° C., overnight. Following hybridization the filters were washed to a final stringency of 6×SSC at 50° C. and exposed to X-OMAT AR film (KODAK, Rochester, N.Y.) at −70° C. The resulting positives were plaque purified by two additional rounds of plating and hybridization. Insert DNA was excised with NotI and ligated into NotI digested pBLUESCRIPT II KS+(STRATAGENE, La Jolla, Calif.). (Genebank #52327) DNA sequences were determined by the SEQUENASE protocol (USBC, Cleveland, Ohio). See Tabor and Richardsaon, J. Biol. Chem. 264 pp 6447–6458. Two clones were isolated in these screens. The human ventricle A1 cDNA (hval-3a) and human ventricle A2a cDNA (hva2-13) contain portions of coding sequences for proteins homologous to the reported dog A1 and A2a cDNAs, respectively. The coding region of the human A1 clone corresponds to nucleotides 482 through 981 (FIG. 2) and is 92% identical to the dog A1 sequence at the nucleotide level. The coding region of the human A2a clone corresponds to nucleotides 497 through 1239 (FIG. 4), and is 90% identical to the dog A2a sequence at the nucleotide level.

STEP B:

The human ventricle A1 adenosine receptor partial cDNA (hvA1-3a) is a 543 bp NotI fragment containing 23 bp 3' untranslated sequence and is 460 bp short of the initiation methionine based on sequence homology to the dog A1 cDNA. A modification of the 5' RACE (rapid amplification of cDNA ends) method (M. A. Frohman et al, (1988), Proc. Natl. Acad. Sci. USA, 85:8998–9002) was used to generate the 5' coding region of the cDNA. First strand cDNA was synthesized from 1 µg of the human ventricle poly(A)⁺RNA in a total volume of 40 µl containing 50 mM Tris, pH 8.0, 140 mM KCl, 10 mM MgCl₂, 10 mM DTT, 15 mM each dNTP, 20 units RNasin (PROMEGA, Madison, Wis.), 20 pmol human primer 79 (see Table I), and 9.2 units AMV reverse transcriptase at 37° C. for 2 hrs. The reaction was then diluted to 120 ml with 0.5 mM Tris, pH 7.6/0.05 mM EDTA and passed through a SEPHACRYL S-300 SPUN COLUMN (PHARMACIA, Piscataway, N.J.). The product in the column effluent was polyadenylated in 100 mM potassium cacodylate, pH 7.2, 2 mM $CoCl_2$, 0.2 mM DTT, 0.15 mM dATP, and 14 units terminal deoxynucleotidyl transferase in a total volume of 31 µl for 10 min. at 37° C. The reaction was terminated by heating at 65° C. for 15 min. and then diluted to 500 µl with 10 mM Tris, pH 8.0/1 mM EDTA (TE).

Ten µl of the poly(A)-tailed first strand cDNA was used as template in a primary PCR amplification reaction according to the GENEAMP protocol (PERKIN ELMER CETUS, Norwalk, Conn.; see Saiki et al. (1988) Science 239:487–491) containing 10 pmol primer 70, 25 pmol primer 71, and 25 pmol human primer 80 (see table I) in a total volume of 50 µl. Primer 70 is 5'-gactcgagtcgacatcga(t)$_{17}$, primer 71 is 5'-gactcgagtcgacatcga, and both are based on M. A. Frohman, et al (1988), Proc. Natl. Acad. Sci. USA, 85:8998–9002. One cycle of PCR was performed of 1 min at 95° C., 2 min at 50° C., 40 min at 72° C., followed by 40 cycles of 40 sec at 94° C., 2 min at 56° C., 3 min at 72° C. The primary PCR amplification reaction product was electrophoresed through a 1.4% agarose gel and an area corresponding to approximately 600 bp was excised. The gel slice was melted and 1 µl was used as template in a secondary PCR amplification reaction containing 100 pmol primer 71 and human primer 81 (see Table I) for 30 cycles of 1 min at 94° C., 2 min at 56° C., 3 min at 72° C. The secondary PCR amplification product was digested with EcoRI and SalI and electrophoresed on a 1.4% agarose gel. An area corresponding to 500–600 bp was excised and ligated into EcoRI/SalI digested pBLUESCRIPT II KS+ (STRATAGENE, La Jolla, Calif.). The sequence of the 515 bp PCR product (5'HVA1-9) was determined by the SEQUENASE protocol (USBC, Cleveland, Ohio). The partial human ventricle A1 cDNA and the PCR product contain overlapping sequence and represent the complete coding region for the human A1 receptor, including 14 and 23 bp of 5' and 3' untranslated sequences, respectively. The sequence of the human A1 adenosine receptor cDNA so identified, is shown in FIG. 2.

STEP C:

A probe was generated by Klenow enzyme extension, including $\alpha^{32}$P-dCTP, of annealed oligonucleotides 62 and 63, and used to screen a human kidney cDNA library (CLONTECH, Palo Alto, Calif.). E. coli strain C600hfl (PROMEGA, Madison, Wis.) was infected with library phage and grown overnight on agar plates at 370C. Phage DNA was transferred to HYBOND-N nylon filters according to the manufacturer's protocol (AMERSHAM, Arlington Heights, Ill.). The probe was incubated with the filters in 750 mM NaCl, 75 mM sodium citrate, 30% formamide, 0.1% sodium dodecyl sulfate, 0.5 mg/mL polyvinylpyrrolidone, 0.5 mg/mL bovine serum albumin, 0.5 mg/mL Ficoll 400, and 0.1 mg/mL salmon sperm DNA, at 42° C. overnight. The filters were washed in 0.9M NaCl and 90 mM sodium citrate at 50° C. A positively hybridizing phage (hkA1-14), was identified and purified by replating and screening with the probe twice more. The final phage plaque was transferred to 0.5 mL 50 mM Tris, pH 7.5, 8 mM $MgSO_4$, 85 mM NaCl, 1 mg/mL gelatin, and 1 µL of a 1:50 dilution in water of the phage stock was used as template for PCR amplification. 50 pmol each of lamL and lamR (Table I) oligonucleotide primers were included, and subjected to 30 cycles of 40 sec at 94° C., 1 min at 55°, 3 min at 72°, then a final 15 min at 72°, according to the GENEAMP protocol (PERKIN ELMER CETUS, Norwalk, Conn.). A 2.0 kb product was identified by agarose gel electrophoresis, and this was subcloned into the EcoRI site of pBLUESCRIPT II KS+ (STRATAGENE, La Jolla, Calif.). Sequence analysis by the SEQUENASE protocol (USBC, Cleveland, Ohio) demonstrated that this cDNA was homologous to the reported dog A1 clone. SmaI and EcoRI digestion released a DNA fragment containing coding sequence from base pair 76 through the translation STOP codon (FIG. 2) that is identical to the human ventricle A1 cDNA sequence (clones hval-3a and 5'hval-9). This fragment was used in construction of the full length coding sequence (see below). The human kidney cDNA also includes about 900 bp of 3' untranslated sequence.

STEP D:

The human ventricle A2a adenosine receptor partial cDNA (hvA2-13) is a 1.6 kb NotI fragment containing approximately 900 bp 3' untranslated sequence and is 496 bp short of the initiation methionine based on sequence homology to the dog A2a cDNA clone. Two consecutive rounds of 5' RACE were utilized to generate the 5' coding region of the cDNA. First strand cDNA was synthesized from 1 µg of the human ventricle poly(A)$^+$RNA in a total volume of 40 µl containing 50 mM Tris, pH 8.0, 140 mM KCl, 10 mM $MgCl_2$, 10 mM DTT, 15 mM each dNTP, 20 units RNasin, 20 pmol human primer 68 or 74 (for 1st or 2nd round RACE respectively), and 9.2 units AMV reverse transcriptase at 37° C. for 2 hrs. The reaction was then diluted to 120 µl with 0.5 mM Tris, pH 7.6/0.05 mM EDTA and passed through a SEPHACRYL S-300 SPUN COLUMN. The products in the column effluents were polyadenylated in 100 mM potassium cacodylate, pH 7.2, 2 mM $CoCl_2$, 0.2 mM DTT, 0.15 mM dATP, and 14 units terminal deoxynucleotidyl transferase in a total volume of 31 µl for 10 min. at 37° C. The poly(A) tailing reaction was terminated by heating at 65° C. for 15 min. and then diluted to 500 µl with TE.

Five or 10 µl (for 1st or 2nd round RACE respectively) of the poly(A) tailed first strand cDNA was used as template in the PCR amplification reaction according to the GENEAMP protocol containing 10 pmol primer 70, 25 pmol primer 71 (primer 70 and 71 sequences are given above), and 25 pmol human primer 69 or 75 (1st or 2nd round RACE respectively; see Table I) in a total volume of 50 µl. One cycle of PCR was performed of 1 min at 95° C., 2 min at 50° C., 40 min at 72° C., followed by 40 cycles of 40 sec at 94° C., 2 min at 56° C., 3 min at 72° C. The PCR amplification products were digested with EcoRI and SalI and electrophoresed on a 1.4% agarose gel. Areas corresponding to 200–400 bp were excised and ligated into EcoRI/SalI digested pBLUESCRIPT II KS+ (STRATAGENE, La Jolla, Calif.). The sequences of the two A2a PCR products, the 332 bp 1st round RACE product (5'hvA2-14) and the 275 bp 2nd round RACE product (5'hvA2-29) were determined by the SEQUENASE (USBC, Cleveland, Ohio) protocol. By sequence homology comparisons with the dog A2a adenosine receptor cDNA sequence, the 1st round RACE product (5'hvA2-14) was 258 bp short of the initiation methionine and the second round RACE product (5'HVA2-29) was determined to extend 1 bp upstream of the initiation methionine. The human ventricle A2a partial cDNA clone (hvA2-13) and the human A2a PCR products (5'hvA2-14 and 5'hva2-29) contain overlapping sequence and together represent the complete coding sequence for the human adenosine A2a receptor, and include 1 bp and 0.8 kb of 5' and 3' untranslated sequence, respectively. The sequence of the human A2a adenosine receptor is shown in FIG. 4.

STEP E:

A double-stranded DNA probe was generated by Klenow enzyme extension, including $\alpha^{32}$P-dCTP, of annealed oligonucleotides 66 and 67, and used to screen a human striata cDNA library (STRATAGENE, La Jolla, Calif.). The oligonucleotide sequence was based on a region of the human ventricle A2a cDNA sequence. *E. coli* strain XL 1-blue (STRATAGENE, La Jolla, Calif.) cells were infected with library phage and grown overnight on agar plates at 37° C. Phage DNA was transferred to HYBOND-N nylon filters according to the manufacturer's protocol (AMERSHAM, Arlington Heights, Ill.). The probe was incubated with the filters in 750 mM NaCl, 75 mM sodium citrate, 10% formamide, 0.5% sodium dodecyl sulfate, 0.5 mg/mL polyvinylpyrrolidone, 0.5 mg/mL bovine serum albumin, 0.5 mg/mL Ficoll 400, and 0.02 mg/mL salmon sperm DNA, at 42° C. overnight. The filters were washed in 0.9M NaCl and 90 mM sodium citrate at 50° C. A positively hybridizing phage (hbA2-22A) was identified and purified by replating and screening with the probe twice more, and subcloned into the plasmid pBLUESCRIPT SK— by the manufacturer's protocol (STRATAGENE, La Jolla, Calif.). See Short et al. (1988) Nucl. Acids Res. 16:7583–7600; Sorge (1988) Strata- gies 1:3–7. The human brain A2a adenosine receptor cDNA (hbA2-22A) spans bp 43 of the A2 coding sequence (FIG. 4) through the translation STOP codon, and includes about 900 bp of 3' untranslated sequence. The sequence of this human brain A2a cDNA is identical to the human ventricle A2a adenosine receptor cDNA (hvA2-13, 5'hvA2-14 and 5'hvA2-29).

STEP F:

A double-stranded DNA probe was generated by Klenow enzyme extension of annealed oligonucleotides 129 and 130, including $\alpha^{32}$P-dCTP, and used to screen a human frontal cortex cDNA library (STRATAGENE, La Jolla, Calif.). The oligonucleotide sequence was based on a region of the human A2a and A1 cDNA sequence. *E. coli* strain XL-1 blue (STRATAGENE, La Jolla, Calif.) cells were infected with library phage and grown overnight at 37° C. Phage DNA was transferred to HYBOND-N nylon filters according to the manufacturer's protocol (AMERSHAM, Arlington Heights, Ill.). The probe was incubated with the filters in 750 mM NaCl, 75 mM sodium citrate, 10% formamide, 0.5% sodium dodecyl sulfate, 0.5 mg/mL polyvinyl-pyrrolidone, 0.5 mg/mL bovine serum albumin, 0.5 mg/mL Ficoll 400, and 0.02 mg/mL salmon sperm DNA, at 42° C. overnight. The filters were washed in 0.9M NaCl and 90 mM sodium citrate at 50° C. A positively hybridizing phage (hb-32c), was identified and purified by replating and screening with the probe twice more. The insert was subcloned to the plasmid pBLUESCRIPT SK—according to the manufacturer's protocol (STRATAGENE, La Jolla, Calif.). Sequence analysis by the SEQUENASE protocol (USBC, Cleveland, Ohio) demonstrated a complete open reading frame coding for amino acid sequence homologous to both of the previously isolated human A1 and A2a clones. This homologous adenosine receptor subtype cDNA is the A2b subtype having the sequences in FIGS. 5A, 5B and 6. A 1.3 kb SmaI-XmnI fragment was ligated into the SmaI site of pSVL (PHARMACIA, Piscataway, N.J.), giving the full length coding sequence of this homologous adenosine receptor in a plasmid suitable for its expression in COS cells. See Sprague et al. (1983) J. Virology 4.5:773; Templeton and Eckhart (1984) Mol. Cell Biol. 4:817.

Table I:

Sequences and directions of the primers used in the isolation of cDNA's and construction of expression plasmids, along with the positions in the clones upon which the sequences are based. Dog A1 and A2a cDNA clones are from F. Libert, et al, (1989) Science 244:569–572. Primers LamL and LamR are based on the sequence of λgt10 (T. V. Hyunh, et al. (1985) DNA Cloning: A Practical Approach, Vol 1, D. Glover, ed, IRL Press, Oxford). The homologous adenosine receptor subtype encoded by the clone hb32C was determined to be the A2b adenosine receptor subtype on the basis of the binding profile of the adenosine receptor agonist NECA and affinities for adenosine receptor antagonists measured on membranes prepared from pSVLhb32C transfected COS7 cells.

| name | sequence | position | clone | direction |
| --- | --- | --- | --- | --- |
| 52 | ATTCGCAGCCACGTCCTGA-GGCGGCGGGAGCCCTTCAA-AGCAGGTGGCACCAGTGCC-CGC (SEQ ID NO. 1) | 1201–1260 | dog A2a | sense |
| 53 | GCGGAGGCTGATCTGCT-CTCCATCACTGCCATGAG-CTGCCAAGGCGCGGGCAC-TGGTGCC (SEQ. ID NO. 2) | 1305–1246 | dog A2a | antisense |
| 62 | TCCAGAAGTTCCGGGTCA-CCTTCCTTAAGATCTGGAA-TGACCACTTCCGCTGCCAGC-CCA (SEQ. ID NO. 3) | 958–1017 | dog A1 | sense |
| 63 | AGTCGTGGGGCGCCTCCT-CTGGGGGGTCCTCGTCGAC-GGGGGGCGTGGGCTGGCAG-CGGA (SEQ ID NO. 4) | 1062–1003 | dog A1 | antisense |
| 66 | GCCTCTTTGAGGATGTGG-TCCCCATGAACTACATGGT-GTACTTCA (SEQ ID NO. 5) | 500–542 | 5'hvA2-14 | sense |
| 67 | GCAGGGGCACCAGCACACA-GGCAAAGAAGTTGAAGTAC-ACCATGT (SEQ ID NO. 6) | 572–528 | 5'hva2-14 | antisense |
| 68 | TCGCGCCGCCAGGAAGAT (SEQ ID NO 7) | 616–599 | hva2-13 | antisense |
| 69 | TATATTGAATTCTAGACAC-CCAGCATGAGC (SEQ ID NO. 8) | 591–574 | hva2-13 | antisense |
| 74 | TCAATGGCGATGGCCAGG (SEQ ID NO. 9) | 303–286 | 5'hva2-14 | antisense |
| 75 | TATATTGAATTCATGGA-GCTCTGCGTGAGG- | 276–259 | 5'hva2-14 | antisense |

| name | sequence | position | clone | direction |
|---|---|---|---|---|
| 79 | GTAGACCATGTACTCCAT (SEQ ID NO. 10) | 560–543 | hva1-3a | antisense |
| 80 | TATATTGAATTCTGACCT-TCTCGAACTCGC- (SEQ ID NO. 11) | 537–521 | hva1-3a | antisense |
| 81 | ATTGAATTCGATCACGGG-CTCCCCCATGC- (SEQ ID NO. 12) | 515–496 | hva1-3a | antisense |
| 129 | ATGGAGTACATGGTCTAC-TTCAACTTCTTTGTGTGGG-TGCTGCCCCCGCT- (SEQ ID NO. 13) | — | — | sense |
| 130 | GAAGATCCGCAAATAGACA-CCCAGCATGAGCAGAAGCG-GGGGCAGCACCC (SEQ ID NO. 14) | — | — | antisense |
| 131 | CCCTCTAGAGCCCAGCCTGT-GCCCGCCATGCCCATCATGG-GCTCC (SEQ ID NO. 15) | 2–19<br>1–14 | 5'hva2-29<br>5'hva1-9 | sense |
| lamL | CCCACCTTTTGAGCAAGTTC (SEQ ID NO. 16) | — | λt10 | — |
| lamR | GGCTTATGAGTATTTCTTCC (SEQ ID NO. 17) | — | λt10 | — |
| 207 | CCCAAGCTTATGAAAGCCAA CAATACC (SEQ ID NO. 27) | | | |
| 208 | TGCTCTAGACTCTGGTATCT TCACATT (SEQ ID NO. 28) | | | |

EXAMPLE 2

Human A1 adenosine receptor expression construct:

To express the human adenosine receptor cDNA in COS cells, the 118bp SalI-SmaI fragment of the human ventricle A1 PCR product (5'HVA1-9) was ligated together with the 1.8 SmaI-EcoRI fragment of the human kidney A1 adenosine receptor cDNA (hkA1-14) and the 3.0 kb SalI-EcoRI fragment of pBLUESCRIPT II KS+, resulting in a plasmid containing the contiguous full length coding sequence for the human A1 adenosine receptor cDNA and some 5' and 3' untranslated sequence. This plasmid was digested first with EcoRI, the resulting ends were filled in by Klenow enzyme extension and then the plasmid was digested with XhoI to release a fragment of 1.9 kb containing the full length human A1 adenosine receptor cDNA. The fragment was subcloned into the expression vector pSVL (PHARMACIA) which had been digested with XhoI-SmaI.

Human A2a adenosine receptor expression construct:

To express the human A2a adenosine receptor cDNA in COS cells, a contiguous A2a cDNA sequence was constructed before subcloning into the expression vector, pSVL. Primer 131, containing an XbaI recognition site, 14 bp of 5' untranslated sequence of human A1 adenosine receptor cDNA, and the first 18 bp of human A2a adenosine receptor cDNA coding sequence was used with primer 75 in PCR with 1 ng of the plasmid containing the human ventricle A2a 2nd round RACE product (5'hvA2-29) as template. Twenty-five cycles of 40 sec at 94° C., 1 min at 55° C., and 3 min at 72° C., then a final incubation of 15 min at 72° C., with 1 ng of plasmid template and 50 pmol of each primer in a volume of 50 μL according to the GENEAMP protocol (PERKIN ELMER CETUS, Norwalk, Conn.), resulted in the expected 302 bp product determined by agarose gel electrophoresis. The 172 bp XbaI-EagI digestion product of this DNA fragment was ligated together with 1125 bp EagI-BglII digestion product of the human striata A2a adenosine receptor cDNA (hbA2–22A) and XbaI-SmaI digested pSVL (PHARMACIA), generating the full length human A2a adenosine receptor cDNA coding sequence in a plasmid suitable for its expression in COS cells.

Mammalian cell expression:

COS7 cells (ATCC #1651-CRL) were grown in complete medium, Dulbecco's modified Eagles's medium, DMEM (GIBCO, Grand Island, N.Y.) containing 10% fetal bovine serum, 100 U/mL penicillin-streptomycin and 2 mM glutamine, in 5% $CO_2$ at 37° C. Transient transfection of COS7 cells was performed by the $CaPO_4$ method (Graham, F. L. and Van Der Erb, A. J. (1973) Virology 52:456–567) using the Mammalian Transfection Kit (STRATAGENE). See Chen and Okayama Mol. Cell Biol. 7:2745–2752. Plasmid DNA (15 μg) was precipitated with 125 mM $CaCl_2$ in BBS (N,N-bis(2-hydroxyethyl)-2-aminoethanesulfonic acid buffered saline) at room temperature for 30 minutes. The DNA precipitate was added to the COS7 cells and incubated for 18 h in 5% $CO_2$ at 37° C. The precipitate was removed and the cells were washed twice with serum free DMEM. Cells were incubated in complete medium in 5% $CO_2$ at 37° C. for 48 h prior to the binding assay.

Stable expression in COS 7 or CHO cells:

To establish stable cell lines, COS7 cells or CHO cells were co-transfected with 20 μg of pSVL containing the adenosine receptor cDNA and 1 μg of pWLneo (STRATAGENE) containing the neomycin gene. See Southern and Berg (1982) J. Mol. App. Gen. 1:327–341. Transfection was performed by the $CaPO_4$ method. DNA was precipitated at room temperature for 30 minutes, added to the COS7 cells and incubated 18 h in 5% $CO_2$ at 37° C. The precipitate was removed and the cells were washed twice with serum free DMEM. Cells were incubated for 24 h in 5% $CO_2$ at 37° C., replated in 24-well dishes at a dilution of 1:10, and incubated an additional 24 h before adding selection medium, DMEM containing 10% fetal bovine serum, 100 U/mL penicillin-streptomycin, 2 mM glutamine and 0.5 mg/mL G418 (GIBCO). Transfected cells were incubated at 5% $CO_2$, 37° C. until viable colonies were visible, approximately 14–21 days. Colonies were selected and propagated. The cell clone with the highest number of human adenosine receptors was selected for subsequent application in the binding assay.

EXAMPLE 3

Binding studies:

Membranes were prepared from transiently transfected COS7 cells 48 h after transfection or from G418-selected stably transfected COS7 or CHO cells. Cells were harvested in 1 mM EDTA in phosphate buffered saline and centrifuged at 2000× g for 10 minutes. The cell pellet was washed once with phosphate buffered saline. The cell pellet was resuspended in 2 mL of 5 mM Tris, pH 7.6/5 mM $MgCl_2$. Membranes were prepared from the cells by freeze-thaw lysis in which the suspension was frozen in a dry ice/ethanol bath and thawed at 25° C. twice. The suspension was homogenized after adding an additional 2 mL of 5 mM Tris, pH 7.6/5 mM $MgCl_2$, in a glass dounce homogenizer with 20 strokes. The membranes were pelleted at 40,000× g at 4° C. for 20 minutes. The membrane pellet was resuspended at a protein concentration of 1–2 mg/mL in binding assay buffer, 50 mM Tris, pH 7.6/10 mM $MgCl_2$. Protein concentration was determined by the method of Bradford ((1976) Anal. Biochem. 72: 248–250). Before the binding assay was performed, the membranes were incubated with adenosine deaminase (BOEHRINGER MANNHEIM), 2 U/mL for 30 minutes at 37° C. Saturation binding of [$^3$H]-cyclohexyladenosine (CHA) was performed on membranes prepared from pSVLA1 transfected COS7 or CHO cells.

Membranes (100 μg) were incubated in the presence of 0.2 U/mL adenosine deaminase with increasing concentrations of CHA (NEN, 32 Ci/mmol) in the range of 0.62–30 Nm for 120 minutes at 25° C. in a total volume of 500 μL. The binding assay was terminated by rapid filtration and three washes with ice-cold 50 mM Tris,pH 7.6/10 mM $MgCl_2$ on a SKATRON CELL HARVESTER equipped with a receptor binding filtermat (SKATRON INSTRUMENTS, INC.). Non-specific binding was determined in the presence of 100 μM $N^6$-cyclopentyladenosine (CPA). Bound radioactivity was measured by scintillation counting in READY SAFE SCINTILLATION COCKTAIL. (BECKMAN). For competition binding experiments, membranes were incubated with 5 Nm [$^3$H]-CHA and various concentrations of A1 adenosine receptor agonists. Saturation binding of [$^3$H] CGS-21680 was performed on membranes prepared from pSVLA2a transfected COS7 cells. Membranes (100 μg) were incubated in the presence of 0.2 U/mL adenosine deaminase with increasing concentrations of CGS21680 (NEN, 48.6 Ci/mmol) in the range of 0.62–80 Nm for 90 minutes at 25° C. in a total volume of 500 μL. The binding assay was terminated by rapid filtration with three washes with ice-cold 50 mM Tris, pH 7.6/10 mM $MgCl_2$ on a Skatron cell harvester equipped with a receptor binding filtermat (SKATRON INSTRUMENTS, INC.). Non-specific binding was determined in the presence of 100 μM CPA. Bound radioactivity was measured by scintillation counting in READY SAFE LIQUID SCINTILLATION COCKTAIL (BECKMAN). For competition binding experiments, membranes were incubated with 5 Nm [$^3$H]-CGS21680 and various concentrations of A2 adenosine receptor agonists.

Saturation binding of [$^3$H]5'-N-ethylcarboxamidoadenosine (NECA) was performed on membranes (100 μg) prepared from pSVLhb32C transfected COS7 cells in the presence of adenosine deaminase with increasing concentrations of NECA (NEN, 15.1 Ci/mmol) in the range of 1.3–106 Nm for 90 minutes at 25° C. in a total volume of 500 μL. The assay was terminated by rapid filtration and three washes with ice-cold binding buffer on a cell harvester equipped with a receptor binding filtermat (SKATRON INSTRUMENTS, INC.). Bound radioactivity was measured by scintillation counting. Non-specific binding was measured on membranes prepared from non-transfected COS7 cells. For competition binding experiments, membranes from transfected cells were incubated with 10 Nm [$^3$H] NECA and varying concentrations of adenosine receptor antagonists.

EXAMPLE 4

The human A3 adenosine receptor was cloned from a human striata cDNA library. Oligonucleotide probes were designed based on the rat A3 sequence of Zhou et al., Proc. Natl. Acad. Sci. 89, 7432 (1992). The complete sequence of the human A3 adenosine receptor was determined and the protein sequence deduced. The cloned human A3 adenosine receptor is expressed in a heterologous expression system in COS and CHO cells. Radiolabeled adenosine receptor agonists and antagonists are used to measure the binding properties of the expressed receptor. Stable cell lines can be used to evaluate and identify adenosine receptor agonists, antagonists and enhancers.

STEP A:

A synthetic probe homologous to the rat A3 adenosine receptor was generated using the polymerase chain reaction (PCR). Three μl of rat brain cDNA was used as template in a PCR amplification reaction according to the GENEAMP protocol (PERKIN ELMER CETUS, Norwalk, Conn.) containing 50 pmol of primers 207 (5'-cccaagcttatgaaagccaa-caatacc) (SEQ. ID NO: 27) and 208 (5'-tgctctagactctggtatct-tcacatt) (SEQ. ID NO: 28) in a total volume of 50 μl. Primers 207 and 208 are based on the published rat A3 adenosine receptor sequence (Zhou, et al, (1992), Proc. Natl. Acad. Sci. USA, 89:7432–7406). Forty cycles of 40 sec at 94° C., 1 min at 55° C., 3 min at 72° C. were performed and the resulting 788 bp fragment was subcloned into HindIII-XbaI digested pBLUESCRIPT II KS+ (STRATAGENE, La Jolla, Calif.). The sequence was verified by the SEQUENASE protocol (USBC, Cleveland, Ohio).

STEP B:

The 788 bp PCR fragment was labeled with $\alpha^{32}$P-dCTP using the MULTIPRIME DNA LABELLING SYSTEM (AMERSHAM, Arlington Heights, Ill.) and used to screen a human striata cDNA library (STRATAGENE, La Jolla, Calif.). E. coli strain XL-1 Blue (STRATAGENE, La Jolla, Calif.) cells were infected with library phage and grown overnight at 37° C. Phage DNA was transferred to HYBOND-N nylon filters according to the manufacturer's protocol (AMERSHAM, Arlington Heights, Ill.). The probe was incubated with the filters in 5×SSC, 30% formamide, 5 ×Denhardt's solution, 0.5% sodium dodecyl sulfate, and 50 μg/ml sonicated salmon testis DNA. The filters were washed in 2×SSC at 55° C. A positively hybridizing phage (HS-21 a) was identified and plaque purified by two additional rounds of plating and hybridization. The insert was subcloned to the plasmid pBLUESCRIPT II SK- according to the manufacturer's protocol (STRATAGENE, La Jolla, Calif.). Upon sequence analysis using the SEQUENASE protocol (USBC, Cleveland, Ohio) it was determined that clone HS-21 a contained the complete open reading frame corresponding to the human homolog of the rat A3 adenosine receptor. The coding region of the human A3 adenosine receptor cDNA is 78% identical to the rat sequence at the nucleotide level and contains 265 bp and 517 bp of 5' and 3' untranslated sequence, respectively. The 1.7 kb fragment was excised using sites present in the multiple cloning site of pBLUESCRIPT II SK- (STRATAGENE, La Jolla, Calif.) and subcloned into Xhol/SacI digested pSVL (PHARMA- CIA, Piscataway, N.J.) for its expression in COS and CHO cells.

EXAMPLE 5

Mammalian cell expression:

COS7 cells (ATCC #1651-CRL) were grown in complete medium, Dulbecco's modified Eagles's medium, DMEM (GIBCO, Grand Island, N.Y.) containing 10% fetal bovine serum, 100 U/mL penicillin-streptomycin and 2 mM glutamine, in 5% $CO_2$ at 37° C. Transient transfection of COS7 cells was performed by the $CaPO_4$ method (Graham, F. L. and Van Der Erb, A. J. (1973) Virology 52:456–567) using the Mammalian Transfection Kit (STRATAGENE). Plasmid DNA (15 µg) was precipitated with 125 mM $CaCl_2$ in BBS (N,N-bis(2-hydroxyethyl)-2-aminoethanesulfonic acid buffered saline) at room temperature for 30 minutes. The DNA precipitate was added to the COS7 cells and incubated for 18 h in 5% $CO_2$ at 37° C. The precipitate was removed and the cells were washed twice with serum free DMEM. Cells were incubated in complete medium in 5% $CO_2$ at 37° C. for 48 h prior to the binding assay.

Stable expression in CHO cells:

To establish stable cell lines, CHO cells were cotransfected with 20 µg of pSVL containing the adenosine receptor cDNA and 1 µg of pWLneo (STRATAGENE) containing the neomycin gene. Transfection was performed by the $CaPO_4$ method. DNA was precipitated at room temperature for 30 minutes, added to the COS7 cells and incubated 18 h in 5% $CO_2$ at 37° C. The precipitate was removed and the cells were washed twice with serum free DMEM. Cells were incubated for 24 h in 5% $CO_2$ at 37° C., replated in 24-well dishes at a dilution of 1:10, and incubated an additional 24 h before adding selection medium, DMEM containing 10% fetal bovine serum, 100 U/mL penicillin-streptomycin, 2 mM glutamine and 1.0 mg/mL G418 (GIBCO). Transfected cells were incubated at 5% $CO_2$, 37° C. until viable colonies were visible, approximately 14–21 days. Colonies were selected and propagated. The cell clone with the highest number of human adenosine receptors was selected for subsequent application in the binding assay.

EXAMPLE 6

Binding assay:

Membranes were prepared from transiently transfected COS7 cells 48 h after transfection or from G418-selected stably transfected CHO cells. Cells were harvested in 1 mM EDTA in phosphate buffered saline and centrifuged at 2000×g for 10 minutes. The cell pellet was washed once with phosphate buffered saline. The cell pellet was resuspended in 2 mL of 5 mM Tris, pH 7.6/5 mM $MgCl_2$. Membranes were prepared from the cells by freeze-thaw lysis in which the suspension was frozen in a dry ice/ethanol bath and thawed at 25° C. twice. The suspension was homogenized after adding an additional 2 mL of 5 mM Tris, pH 7.6/5 mM $MgCl_2$, in a glass dounce homogenizer with 20 strokes. The membranes were pelleted at 40,000×g at 4° C. for 20 minutes. The membrane pellet was resuspended at a protein concentration of 1–2 mg/mL in binding assay buffer, 50 mM Tris, pH 7.6/10 mM $MgCl_2$. Protein concentration was determined by the method of Bradford ((1976) Anal. Biochem. 72: 248–250). Before the binding assay was performed, the membranes were incubated with adenosine deaminase (BOEHRINGER MANNHEIM), 2 U/mL for 30 minutes at 37° C. Saturation binding of $[^{125}I]$-$N^6$-aminobenzyladenosine ($^{125}I$-ABA) or $[^{125}I]$-$N^6$-2-(4-amino-3-iodophenyl)ethyladenosine (APNEA) was performed on membranes prepared from pSVLA3 transfected COS7 cells. Membranes (100 µg) were incubated in the presence of 0.2 U/mL adenosine deaminase with increasing concentrations of $^{125}I$-ABA in the range of 0.1–30 Nm for 120 minutes at 25° C. in a total volume of 500 µL. The binding assay was terminated by rapid filtration and three washes with ice-cold 50 mM Tris, pH 7.6/10 mM $MgCl_2$ on a Skatron cell harvester equipped with a receptor binding filtermat (SKATRON INSTRUMENTS, INC.). Non-specific binding was determined on non-transfected cells. Bound radioactivity was measured by scintillation counting in Ready Safe Scintillation Cocktail (BECKMAN).

EXAMPLE 7

In vitro transcription and oocyte expression:

The 1.3 kb XhoI-BamHI fragment of the pSVL expression construct (described in Example 2) containing the full length human A2a adenosine receptor coding sequence was ligated into SalI-SpeI digested pGEMA (Swanson, et al, (1990) Neuron 4:929–939). The resulting plasmid, pGEMA2, was linearized with NotI, forming a template for in vitro transcription with T7 RNA polymerase. The homologous adenosine receptor subtype cDNA in pBluescript SK- was used as a template for in vitro transcription by T3 polymerase after removal of most of the 5' untranslated region, with the exception of 20 bp, as a 0.3 kb SmaI fragment. The $K^+$ channel cDNA, Kv3.2b was employed as a negative control in the cAMP accumulation assay. The generation of Kv3.2b RNA was described by Luneau, et al, ((1991) FEBS Letters 1:163–167). Linearized plasmid templates were used with the STRATAGENE mCAP kit according to the manufacturer's protocol, except that the SP6 RNA polymerase reaction was performed at 40° C. Oocytes were harvested from mature female *Xenopus laevis*, treated with collagenase, and maintained at 18° C. in ND96 medium (GIBCO) supplemented with 1 mM sodium pyruvate and 100 µg/mL gentamycin. Fifty nanoliters (10 ng) of RNA diluted in $H_2O$ was injected and oocytes were incubated at 18° C. for 48 hours.

EXAMPLE 8 cAMP accumulation assay in oocytes:

Oocytes injected with either human adenosine receptor transcript or the Kv3.2b transcript were transferred to fresh medium supplemented with 1 mM of the phosphodiesterase inhibitor, Ro 20-1724 (RBI, Natick, Mass.) and 1 mg/mL bovine serum albumin incubated for 30 minutes and transferred to an identical medium with or without the agonist adenosine (10 mM) for an additional 30 minutes at room temperature. Groups of 5–10 oocytes were lysed by transfer to ND96/100 mM HCl/1 mM Ro 20-1724 in microfuge tubes, shaken, incubated at 95° C. for 3 min, and centrifuged at 12000 g for 5 min. Supernatants were stored at −70° C. before cAMP measurements. Cyclic AMP levels were determined by radioimmunoassay (RIANEN kit, DuPont/NEN) using the acetylation protocol. The adenosine receptor antagonist, 8-(p-sulfophenyl)theophylline (100 µM) was utilized to inhibit the cAMP response induced by adenosine in oocytes expressing the adenosine receptors.

EXAMPLE 9 cAMP accumulation in stable CHO cell lines:

The changes in cAMP accumulation can alternatively be measured in stably transfected CHO cells expressing the human adenosine receptor subtypes. CHO cells are washed twice in phosphate buffered saline (PBS) and detached in 0.2% EDTA in PBS. The cells are pelleted at 800 rpm for 10 min and resuspended in KRH buffer (140 mM NaCl/5 mM KCl/2 mM $CaCl_2$/1.2 mM $MgSO_4$/1.2 mM $KH_2PO_4$/6 mM glucose/25 mM Hepes buffer, pH 7.4). The cells are washed once in KRH buffer and resuspended at $10^7$ cells/mL. The cell suspension (100 μL) is mixed with 100 μL of KRH buffer containing 200 μM Ro 20-1724 and incubated at 37° C. for 10 minutes. Adenosine (10 μM) was added in 200 μL KRH buffer containing 200 μM Ro 20-1724 and incubated at 37° C. for 20 minutes. After the incubation, 400 μL of 0.5 mM NaOAc (pH 6.2) was added and the sample was boiled for 20 minutes. The supernatant was recovered by centrifugation for 15 minutes and stored at −70° C. cAMP levels were determined by radioimmunoassay (RIANEN kit, DuPont/NEN) using the acetylation protocol. The effect of antagonists on cAMP accumulation are measured by preincubation for 20 minutes before adding adenosine. Results show highly sensitive measurement of cAMP accumulation in response to adenosine (ADO) in a stable CHO cell line expressing the human A2b receptor and the effect of the antagonist 1,3-diethyl-8-phenylxanthine (DPX).

While the foregoing specification teaches the principles of the present invention, with examples provided for the purpose of illustration, it will be understood that the practice of the invention encompasses all of the usual variations, adaptations, modifications, as come within the scope of the following claims and its equivalents.

What is claimed is:

1. A human adenosine receptor binding assay for a test sample using a mammalian cell line transfected with a plasmid, which plasmid comprises a mammalian expression vector and the nucleotide sequence encoding a human adenosine receptor protein, the assay comprising the steps of:

(1) expressing a human adenosine receptor protein, encoded by the nucleotide sequence, in a transfected cell line selected from COS7 cells transfected with the plasmid or CHO cells transfected with the plasmid;

(2) forming a membrane preparation from the cells;

(3) mixing a test sample with the membrane preparation and a radioactive ligand;

(4) incubating the mixture of Step (3);

(5) separating the radioactive ligand bound to the human adenosine protein from unbound radioactive ligand; and (6) measuring the radioactivity of the radioactive ligand bound to the adenosine receptor protein;

wherein the adenosine receptor protein is the A2b human adenosine receptor protein.

\* \* \* \* \*